United States Patent
Ozawa

(10) Patent No.: US 12,061,164 B2
(45) Date of Patent: Aug. 13, 2024

(54) GAS SENSOR

(71) Applicant: DENSO CORPORATION, Kariya (JP)

(72) Inventor: Masato Ozawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 669 days.

(21) Appl. No.: 16/799,998

(22) Filed: Feb. 25, 2020

(65) Prior Publication Data
US 2020/0191743 A1 Jun. 18, 2020

Related U.S. Application Data

(63) Continuation of application No. PCT/JP2018/031518, filed on Aug. 27, 2018.

(30) Foreign Application Priority Data

Aug. 31, 2017 (JP) .................. 2017-167558

(51) Int. Cl.
| | | |
|---|---|---|
| *G01N 27/406* | (2006.01) | |
| *G01N 27/409* | (2006.01) | |
| *G01N 33/00* | (2006.01) | |
| *H01R 13/24* | (2006.01) | |

(52) U.S. Cl.
CPC ..... *G01N 27/4062* (2013.01); *G01N 27/4067* (2013.01); *G01N 27/409* (2013.01); *G01N 33/0036* (2013.01); *H01R 13/2407* (2013.01); *H01R 2201/20* (2013.01)

(58) Field of Classification Search
CPC .......... G01N 27/4062; G01N 27/4067; G01N 27/409; G01N 27/407–4071; G01N 33/0036; H01R 13/2407; H01R 2201/20
See application file for complete search history.

(56) References Cited

U.S. PATENT DOCUMENTS

| | | |
|---|---|---|
| 5,922,938 A | 7/1999 | Hafele |
| 2001/0025522 A1 | 10/2001 | Kojima |

(Continued)

FOREIGN PATENT DOCUMENTS

| | | |
|---|---|---|
| JP | 2006-337096 | 12/2006 |
| JP | 2012-230076 | 11/2012 |

(Continued)

*Primary Examiner* — James Lin
*Assistant Examiner* — Vivian A Tran
(74) *Attorney, Agent, or Firm* — Nixon & Vanderhye, PC

(57) ABSTRACT

A gas sensor includes a sensor element, spring terminals, and a spring insulator. The spring terminals are formed of bendable wire. The spring insulator includes an insertion hole in which a proximal section of the sensor element is inserted and retaining grooves, which communicate with the insertion hole. The spring terminals each include a holding section retained in the associated retaining groove and an arm section, which extends from the holding section and comes into contact with the associated one of terminal contact portions of the sensor element while flexing with respect to the holding section. When viewed in an insertion direction of the sensor element to the insertion hole, a flexing direction of the arm section of each spring terminal with respect to the holding section is inclined with respect to the outer surface of the associated terminal contact portion.

14 Claims, 16 Drawing Sheets

(56) References Cited

U.S. PATENT DOCUMENTS

| | | | |
|---|---|---|---|
| 2003/0074950 A1* | 4/2003 | Yamada | G01N 27/4075 |
| | | | 73/31.05 |
| 2004/0175992 A1* | 9/2004 | Kimata | H01R 12/721 |
| | | | 439/637 |
| 2007/0113617 A1 | 5/2007 | Yamauchi | |
| 2013/0305811 A1 | 11/2013 | Noda et al. | |
| 2017/0179629 A1 | 6/2017 | Hino | |

FOREIGN PATENT DOCUMENTS

| | | | |
|---|---|---|---|
| JP | 2012230076 A * | 11/2012 | |
| JP | 2015-145831 | 8/2015 | |
| WO | WO-2015115660 A1 * | 8/2015 | G01N 27/4062 |

* cited by examiner

GAS SENSOR

CROSS-REFERENCE TO RELATED APPLICATION

This application is a U.S. application under 35 U.S.C. 111(a) and 363 that claims the benefit under 35 U.S.C. 120 from International Application No. PCT/JP2018/031518 filed on Aug. 27, 2018, the entire contents of which are incorporated herein by reference. This application is also based on Japanese Patent Application No. 2017-167558 filed Aug. 31, 2017, the description of which is incorporated herein by reference.

BACKGROUND

Technical Field

The present disclosure relates to a gas sensor.

Background Art

A gas sensor is used for detecting the concentration of, for example, oxygen or a specific gas component in exhaust gas discharged from an internal combustion engine. A sensor element of the gas sensor includes a laminated sensor element in which insulation layers are laminated on a plate-like solid electrolyte. The insulation layers form a gas chamber into which exhaust gas is introduced. The end of the laminated sensor element is accommodated in an insertion hole of an insulator and is electrically connected to spring terminals retained in retaining grooves of the insulator.

More specifically, the spring terminals each include a holding section and an arm section, which flexes with respect to the holding section and is in contact with the sensor element. The spring terminals are located on both sides of the sensor element, so that when the arm sections come into contact with the sensor element and flex, the arm sections sandwich the sensor element from both sides. Additionally, terminal contact portions, which are connected to electrodes located on the solid electrolyte, are located on the outer surfaces of the sensor element. The arm sections of the spring terminals come into contact with the terminal contact portions, so that the electrodes of the sensor element are electrically connected to the outside of the gas sensor through the spring terminals.

SUMMARY

One aspect of the present disclosure provides a gas sensor including a sensor element, spring terminals, and an insulator. The sensor element for detecting gas includes terminal contact portions. The insulator includes an insertion hole and retaining grooves. Each spring terminal includes a holding section, which is retained in the associated retaining groove, and an arm section. As viewed in an insertion direction of the sensor element into the insertion hole, at least one of the spring terminals includes an inclined spring terminal, and a flexing direction of the arm section of the inclined spring terminal with respect to the holding section is inclined with respect to an outer surface of the associated terminal contact portion.

Reference signs in parentheses given to components in one aspect of the present disclosure indicate the correspondence to reference signs in the drawing of the embodiment and do not limit the components to only the contents of the embodiment.

BRIEF DESCRIPTION OF THE DRAWINGS

The object, features, advantages, and the like of the present disclosure will become more apparent by the following detailed description with reference to the accompanying drawings in which.

DETAILED DESCRIPTION OF THE PREFERRED EMBODIMENTS

Figure 1:
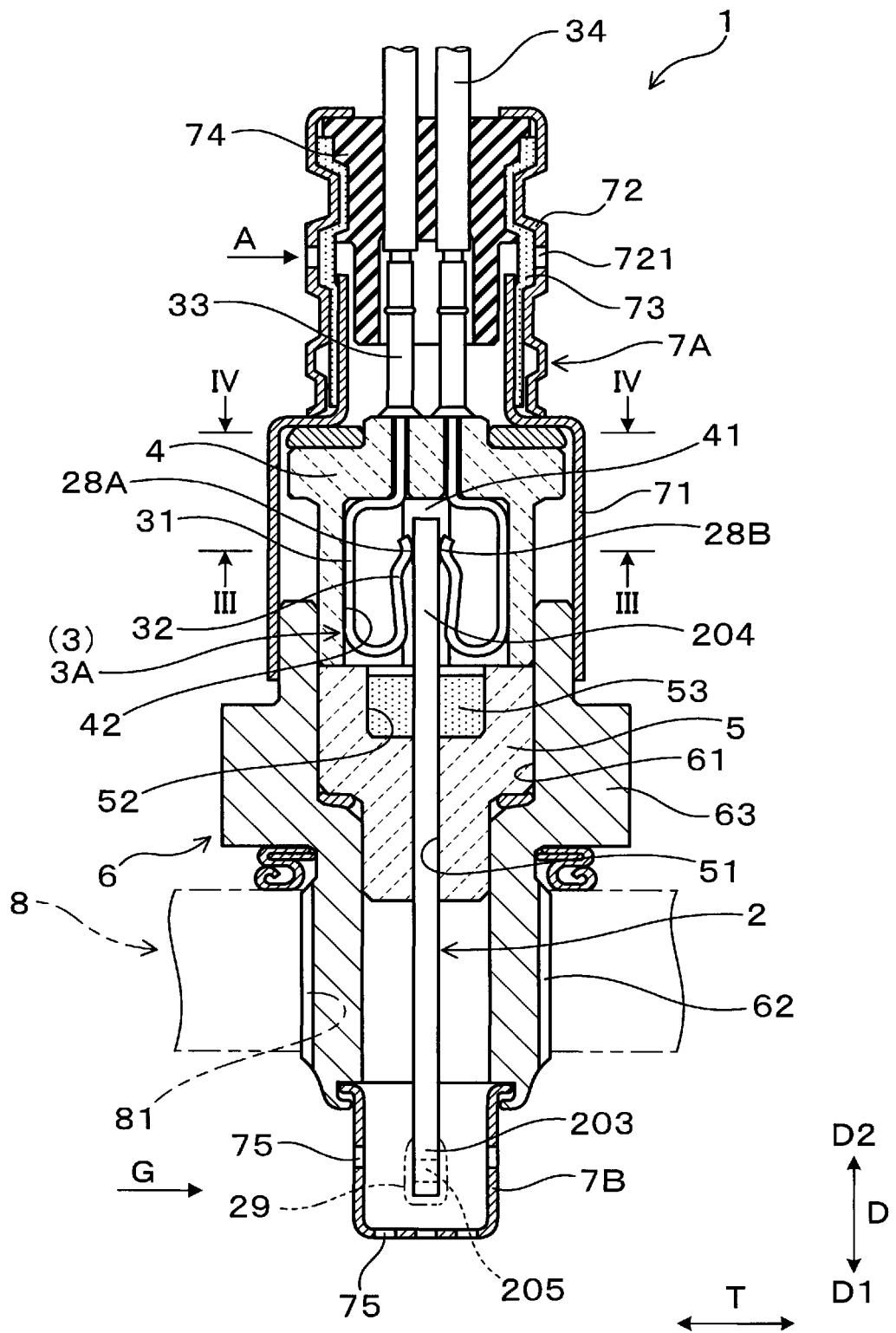
FIG. 1 is a cross-sectional view of a gas sensor according to a first embodiment.

The inventor of the present disclosure has studied a gas sensor that has a favorable electrical connection state between spring terminals and a sensor element.

Due to the constraints when mounting on, for example, a vehicle, there is a demand for a reduction in the size of the gas sensor. Given the circumstances, the spring terminals are formed of a wire material, gaps between the spring terminals are reduced, and the size of the outer shape of the insulator is reduced. For example, JP 2015-145831 A discloses a gas sensor that uses spring terminals formed of a wire material.

When the gas sensor is assembled, the end of the sensor element is inserted in the insertion hole of the insulator, in which the spring terminals are retained in the respective retaining grooves. However, the arm sections of the spring terminals disclosed in, for example, PTL 1 contacts the terminal contact portions on the outer surfaces of the sensor element perpendicularly and flex with respect to the holding sections. The flexing direction of the arm sections is the thickness direction of the sensor element and is perpendicular to the outer surfaces of the terminal contact portions.

Thus, if the arm sections slide on the outer surfaces of the terminal contact portions during flexing, the arm sections may possibly be displaced either to the left or right with respect to the electrode contact portions. As a result, the contact positions of the arm sections with respect to the terminal contact portions are apt to change, and contact failure may possibly occur between the arm sections and the terminal contact portions. Consequently, a further change is necessary to improve the state of the electrical connection between the spring terminals and the sensor element.

The present disclosure is intended to provide a gas sensor that has a favorable electrical connection state between spring terminals and a sensor element.

One aspect of the present disclosure provides a gas sensor including a sensor element, spring terminals, and an insulator. The sensor element includes terminal contact portions located on outer surfaces of a proximal section of the sensor element. The sensor element detects gas. The spring terminals are formed of bendable wire. The insulator includes an insertion hole in which the proximal section of the sensor element is inserted and retaining grooves, which communicate with the insertion hole. Each spring terminal includes a holding section, which is retained in the associated retaining groove, and an arm section, which extends from the holding section and comes into contact with the associated terminal contact portion while flexing with respect to the holding section. As viewed in an insertion direction of the sensor element into the insertion hole, at least one of the spring terminals includes an inclined spring terminal, and a flexing direction of the arm section of the inclined spring terminal with respect to the holding section is inclined with respect to an outer surface of the associated terminal contact portion.

According to the gas sensor of the one aspect, the flexing direction of the arm sections of the spring terminals retained in the insulator is changed. More specifically, as viewed in the insertion direction of the sensor element into the insertion hole, the flexing direction of the arm section with respect to the holding section in at least one of the spring terminals is inclined with respect to the outer surface of the associated terminal contact portion.

When the sensor element is inserted in the insertion hole of the insulator, the arm section flexes in a direction inclined with respect to the outer surface of the associated terminal contact portion. When the arm section slides on the outer surface of the associated terminal contact portion, the direction in which the arm section slides is restricted. More specifically, the arm section slides in a direction such that the inclination angle with respect to the normal to the outer surface of the terminal contact portion is increased.

This determines the contact position of the arm section with respect to the terminal contact portion, so that contact failure between the arm section and the terminal contact portion is less likely to occur. Consequently, according to the gas sensor of the one aspect, the state of the electrical connection between the spring terminals and the sensor element is favorable.

The gas sensor according to a preferred embodiment will be described with reference to the drawings.

First Embodiment

Figure 2:
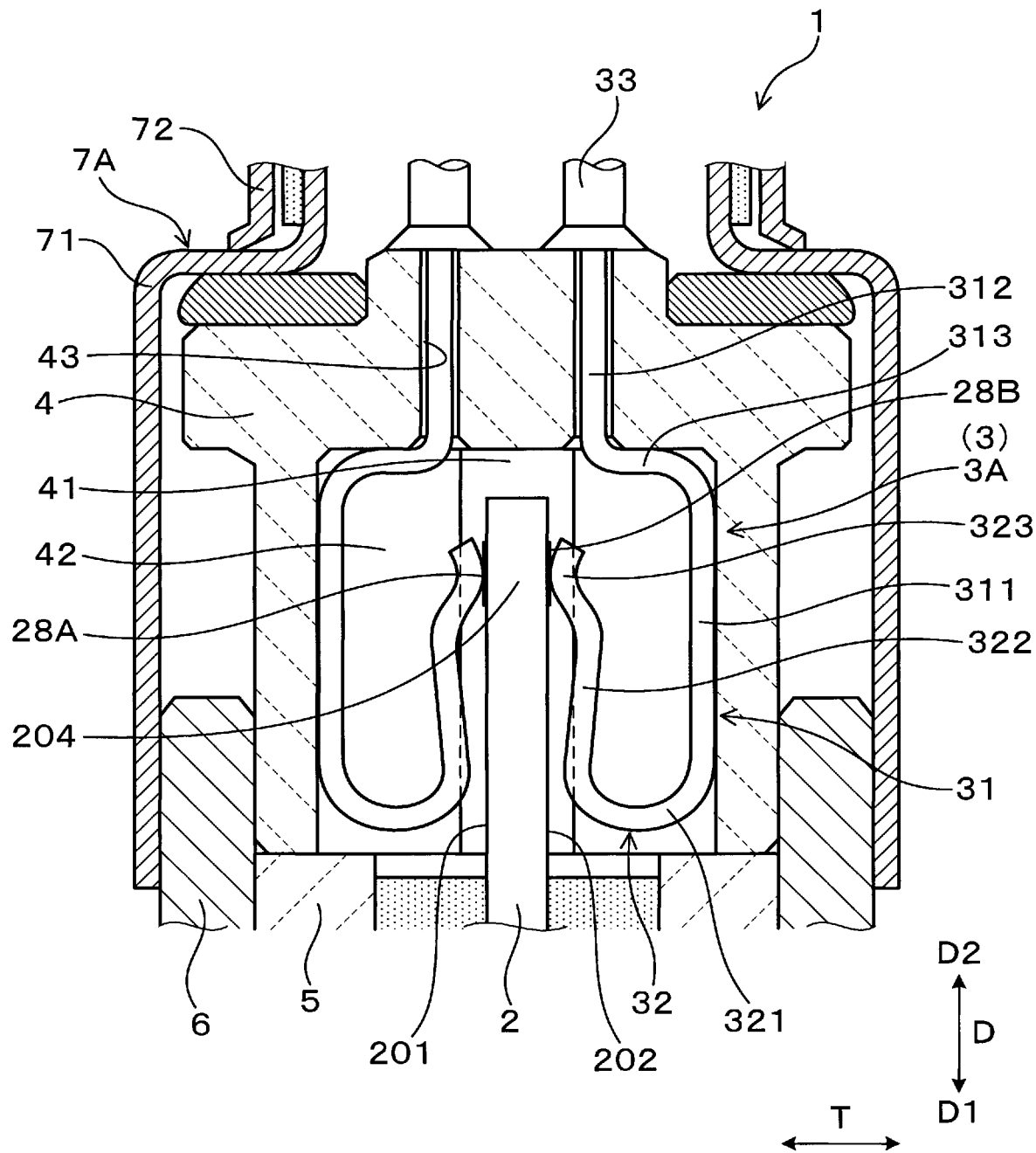
FIG. 2 is an enlarged cross-sectional view illustrating spring terminals of the gas sensor and their surroundings according to the first embodiment.

A gas sensor 1 of the present embodiment includes, as shown in FIGS. 1 and 2, a sensor element 2, spring terminals 3, and a spring insulator 4. The sensor element 2 is for detecting gas. Terminal contact portions 28A and 28B are provided on outer surfaces 201 and 202 of a proximal section 204 of the sensor element 2. The spring terminals 3 are formed of bendable wire. The spring insulator 4 includes an insertion hole 41, in which the proximal section 204 of the sensor element 2 is inserted, and retaining grooves 42, which communicate with the insertion hole 41.

Figure 3:
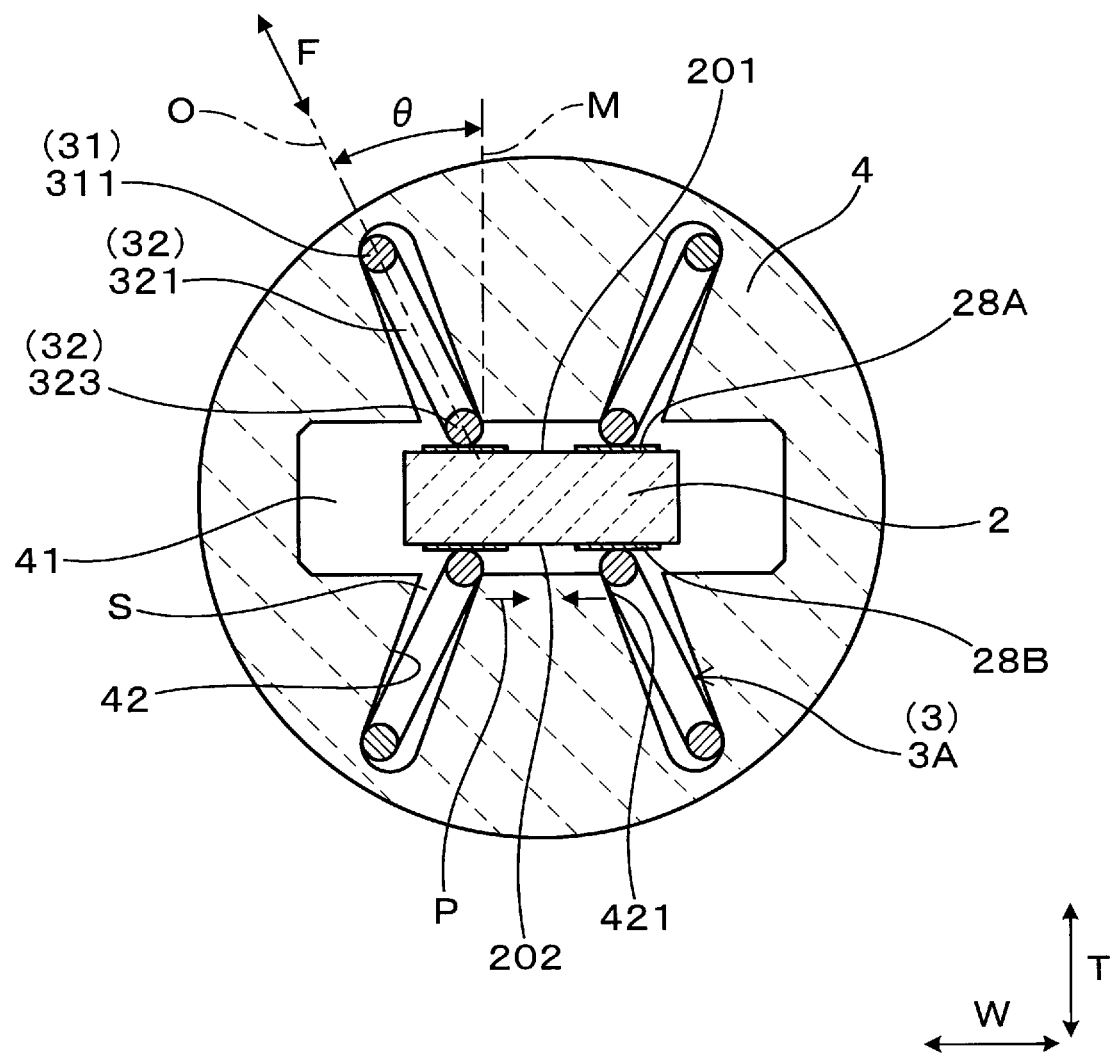
FIG. 3 is a cross-sectional view taken along line III-III of FIG. 1 viewed from the direction of arrows illustrating the spring terminals of the gas sensor and their surroundings according to the first embodiment.

As shown in FIG. 2, the spring terminals 3 each include a holding section 31, which is held in the associated retaining groove 42, and an arm section 32, which extends from the holding section 31. The arm sections 32 is in contact with the terminal contact portions 28A and 28B while flexing with respect to the holding sections 31. As shown in FIG. 3, when viewed in an insertion direction D of the sensor element 2 into the insertion hole 41, a flexing direction F of the arm section 32 of an inclined spring terminal 3A, which is at least one of the spring terminals 3, with respect to the holding section 31 is inclined with respect to the outer surface of the associated one of the terminal contact portions 28A and 28B.

All the spring terminals 3 of the present embodiment are inclined spring terminals 3A. The outer surfaces of the terminal contact portions 28A and 28B refer to the surfaces parallel to the outer surfaces 201 and 202 of the sensor element 2.

Hereinafter, the gas sensor 1 of the present embodiment will be described.

(Internal Combustion Engine)

As shown in FIG. 1, the gas sensor 1 of the present embodiment is located on a pipe 8 of an exhaust system of a vehicle internal combustion engine (engine) and detects oxygen or a specific gas component in exhaust gas G that flows through the pipe 8. The gas sensor 1 may be located upstream of a section where a catalyst is located in the pipe 8 and may also be located downstream of the section where the catalyst is located in the pipe 8. The pipe 8 in which the gas sensor 1 is located may be a pipe on an intake side of a forced induction device, which increases the pressure of the air that the internal combustion engine takes in using the exhaust gas G. Alternatively, the pipe 8 in which the gas sensor 1 is located may be a pipe of an exhaust recirculation mechanism, which recirculates some of the exhaust gas G discharged to the exhaust passage from the internal combustion engine to an intake passage of the internal combustion engine.

The vehicle equipped with the pipe 8 in which the gas sensor 1 is located may be a typical vehicle that travels using fuel, a vehicle that stops idling when stopped, or a hybrid vehicle. The gas sensor 1 may be an oxygen concentration cell sensor that detects an electromotive force generated between a pair of electrodes or a limiting current sensor that utilizes limiting current characteristics caused when voltage is applied between a pair of electrodes.

The gas sensor 1 of the present embodiment is used for detecting the air-fuel ratio of the internal combustion engine obtained from the exhaust gas G as application for detecting gas. Besides the above, the gas sensor 1 may be used for detecting a specific gas component such as NOx, detecting the oxygen concentration of the exhaust gas G discharged from the internal combustion engine, and detecting whether the air-fuel ratio of the internal combustion engine obtained from the exhaust gas G is in a fuel-rich condition or in a fuel-lean condition with respect to a stoichiometric air-fuel ratio.

(Sensor Element 2)

Figure 4:
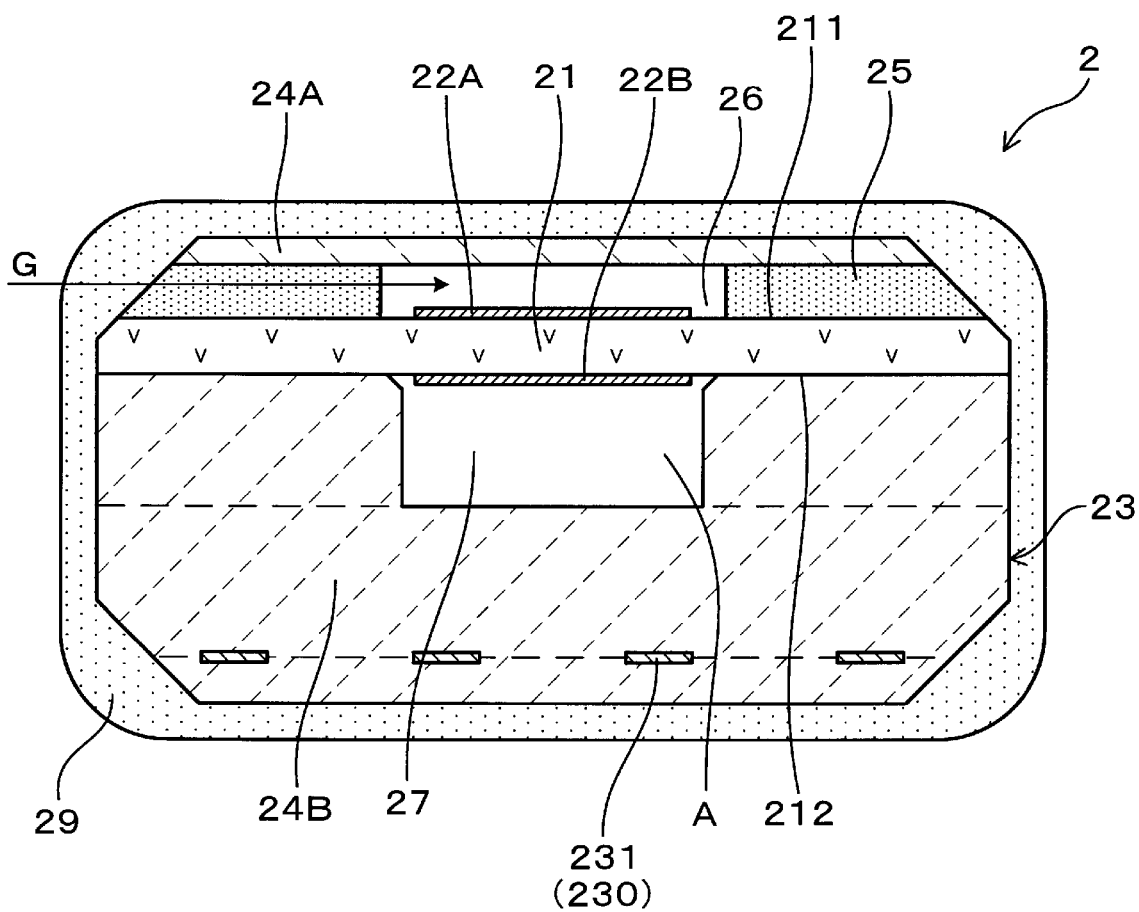
FIG. 4 is a cross-sectional view of a sensor element according to the first embodiment.
Figure 5:
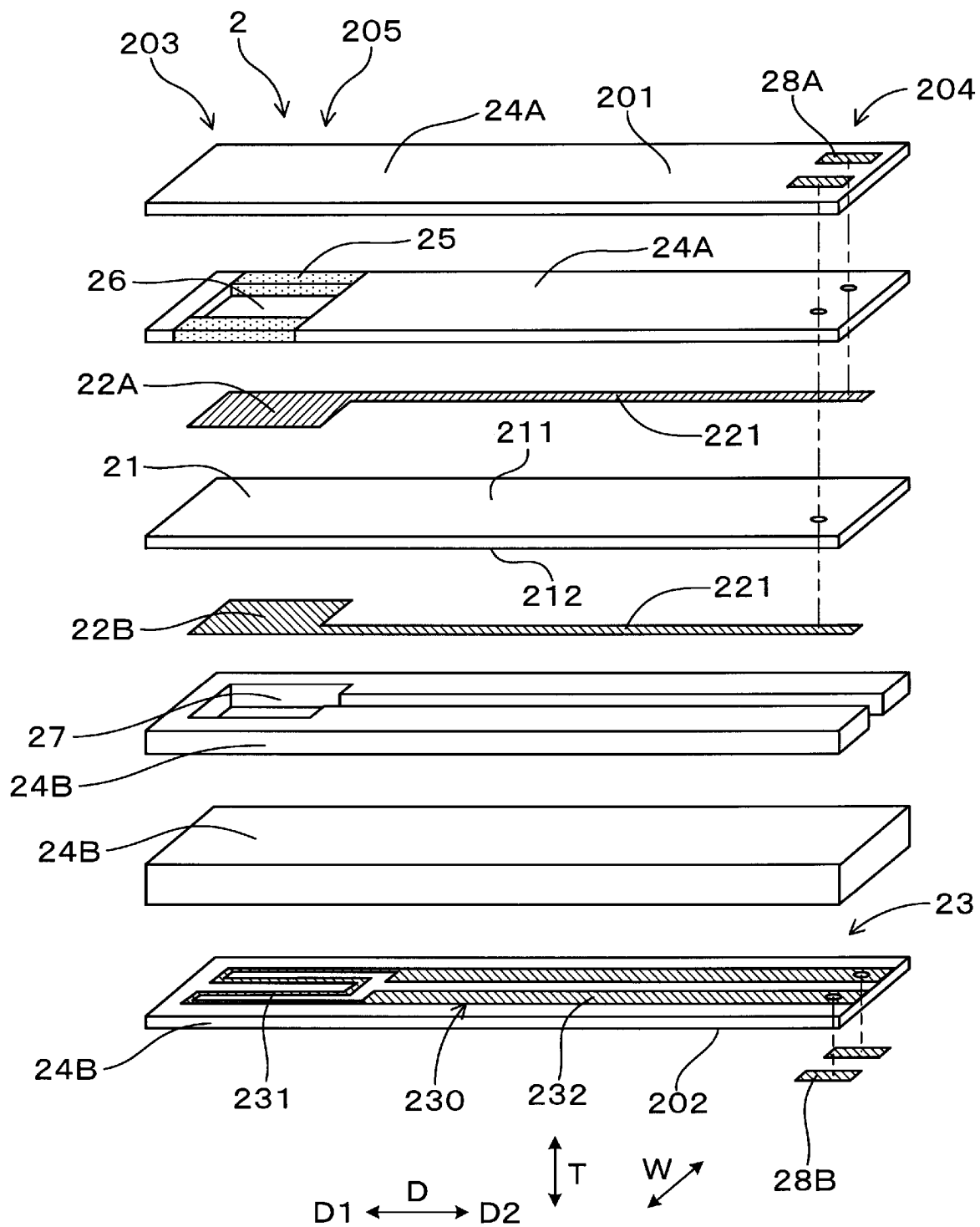
FIG. 5 is an exploded perspective view of the sensor element of the first embodiment.

As shown in FIGS. 4 and 5, the sensor element 2 includes a plate-like solid electrolyte 21, on which a pair of electrodes 22A and 22B are located, and a heater 23, which is laminated on the solid electrolyte 21. A detection electrode 22A, which is exposed to the exhaust gas G, is located on a first main surface 211 of the solid electrolyte 21, and a reference electrode 22B, which is exposed to air A, is located on a second main surface 212 of the solid electrolyte 21. A gas chamber 26, to which the exhaust gas G is introduced, is formed adjacent to the first main surface 211 of the solid electrolyte 21 by an insulation layer 24A, which is laminated on the first main surface 211. The detection electrode 22A is located in the gas chamber 26. An air duct 27, to which the air A is introduced, is formed adjacent to the second main surface 212 of the solid electrolyte 21 by an insulation layer 24B of the heater 23, which is laminated on the second main surface 212. The reference electrode 22B is located in the air duct 27.

Part of the insulation layer 24A, which defines the gas chamber 26, is formed as a porous diffusion resistance layer 25, which has the properties of permitting the exhaust gas G to pass through. The diffusion resistance layer 25 introduces the exhaust gas G to the gas chamber 26 at a constant diffusion speed. The gas sensor 1 of the present embodiment constitutes an air-fuel ratio sensor, and a voltage for exhibiting limiting current characteristics is applied between the detection electrode 22A and the reference electrode 22B. The gas chamber 26 is formed at a distal end section 203 of the sensor element 2, and the air duct 27 is formed to extend from the distal end section 203 of the sensor element 2 to the end surface of the proximal section 204. The air A that enters the gas sensor 1 is introduced to the air duct 27.

As shown in FIG. 5, the heater 23 includes a heating element 230 embedded in the insulation layer 24B. The heating element 230 includes a heating portion 231, which is heated by the application of electrical power, and a pair of lead portions 232, which are connected to the heating portion 231. The heating portion 231 is located at a position facing the detection electrode 22A and the reference electrode 22B, and the pair of lead portions 232 extend from the heating portion 231 to the proximal section 204 of the sensor element 2. A lead portion 221 connected to the detection electrode 22A and a lead portion 221 connected to the reference electrode 22B extend to the proximal section 204 of the sensor element 2.

The sensor element 2 is formed to have an elongated shape. The insertion direction D of the sensor element 2 extends in the longitudinal direction of the sensor element 2. A detector 205, which is constituted by the detection electrode 22A, the reference electrode 22B, the gas chamber 26, and the diffusion resistance layer 25, is formed on the distal end section 203 of the sensor element 2 in the longitudinal direction. The terminal contact portions 28A and 28B are formed on the outer surfaces 201 and 202 of the proximal section 204 of the sensor element 2 in the longitudinal direction. As shown in FIGS. 1 and 4, a porous protection layer 29 is provided on the outer circumference of the distal end section 203 of the sensor element 2 to cover the detector 205.

In the sensor element 2, the direction in which the terminal contact portions 28A and 28B are located to face the spring terminals 3 is referred to as a thickness direction T, and the direction orthogonal to the insertion direction D and the thickness direction T is referred to as a widthwise direction W. The thickness direction T is a direction in which the detection electrode 22A and the reference electrode 22B are located to face each other on the solid electrolyte 21. The insertion direction D, the thickness direction T, and the widthwise direction W are directions common among, for example, the sensor element 2, the spring insulator 4, and the gas sensor 1. The insertion direction D points opposite directions. In FIGS. 1, 2, 5, and 6, the distal direction of the insertion direction D is denoted by D1, and the proximal direction of the insertion direction D is denoted by D2.

Figure 6:
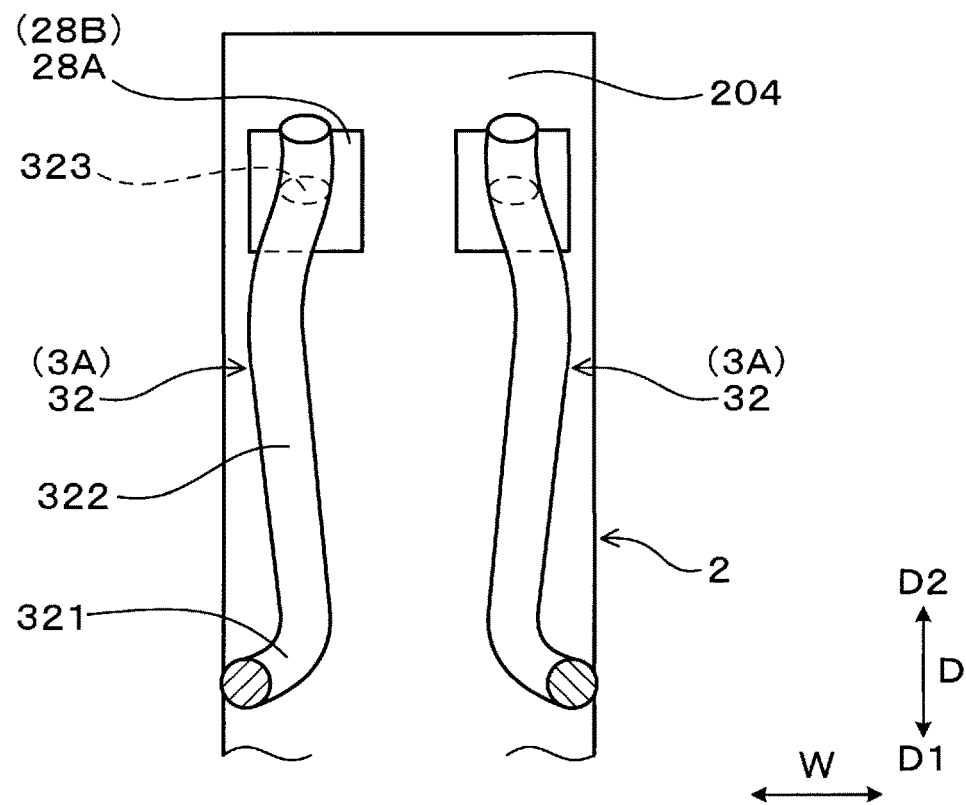
FIG. 6 is an explanatory diagram illustrating terminal contact portions on an outer surface of the sensor element and their surroundings according to the first embodiment as viewed from the thickness direction of the sensor element.

As shown in FIGS. 3, 5, and 6, the terminal contact portions 28A and 28B on the proximal section 204 of the sensor element 2 are located side by side in the widthwise direction W, which is orthogonal to the insertion direction D. The terminal contact portions 28A and 28B are located on the outer surfaces 201 and 202 on both sides of the sensor element 2 in the thickness direction T. The terminal contact portions 28A and 28B are constituted by two first terminal contact portions 28A, which are respectively connected to the lead portion 221 of the detection electrode 22A or the lead portion 221 of the reference electrode 22B, and two second terminal contact portions 28B, which are connected to the lead portions 232 of the heating element 230. In the present embodiment, the two first terminal contact portions 28A are located on the first outer surface 201 of the sensor element 2 side by side in the widthwise direction W, and the two second terminal contact portions 28B are located on the second outer surface 202 of the sensor element 2 side by side in the widthwise direction W. The first outer surface 201 is the outer surface located on the side of the solid electrolyte 21 on which the detection electrode 22A is provided, and the second outer surface 202 is the outer surface located on the side of the solid electrolyte 21 on which the reference electrode 22B is provided.

In the present embodiment, the insulation layer 24A is formed along the entire length of the solid electrolyte 21 in the longitudinal direction. The first outer surface 201 and the second outer surface 202 of the sensor element 2 are the outer surfaces of the insulation layers 24A and 24B. If the insulation layer 24A is formed in the region including the distal end section 203 of the sensor element 2 and is not formed on the proximal section 204 of the sensor element 2, the first outer surface 201 may be constituted by the outer surface of the solid electrolyte 21.

The electrodes 22A and 22B are formed of material containing noble metal that has catalytic activity to oxygen, and the solid electrolyte 21 is formed of a zirconia material that has oxygen-ion conductivity. The insulation layers 24A and 24B and the diffusion resistance layer 25 are formed of an alumina material, which is an insulating ceramic.

(Element Insulator 5)

As shown in FIG. 1, an element insulator 5 in which the sensor element 2 is inserted and retained and the spring insulator 4 for retaining the spring terminals 3 are located in the gas sensor 1. The element insulator 5 is also called as insulator glass and is formed of an insulating ceramic such as alumina. The element insulator 5 is formed by compressing ceramic powder. The element insulator 5 includes a placement hole 51 for the sensor element 2 to be placed. The placement hole 51 extends through the element insulator 5 in the insertion direction D. The intermediate position of the sensor element 2 in the longitudinal direction is located in the placement hole 51. The sensor element 2 is secured to the element insulator 5 by, for example, a glass material 53 that fills a recess 52 formed at the proximal section of the placement hole 51.

(Housing 6)

As shown in FIG. 1, a housing 6 includes a housing hole 61, which extends through the housing 6 in the insertion direction D. The element insulator 5 is located in the housing hole 61. Additionally, a thread portion 62 and a hexagonal flange portion 63 are formed along the entire outer circumference of the housing 6. The thread portion 62 and the hexagonal flange portion 63 are for mounting the gas sensor 1 on the pipe 8 with the gas sensor 1 being inserted in a mounting hole 81 of the pipe 8.

(Wiring Cover 7A and Element Cover 7B)

As shown in FIG. 1, a wiring cover 7A, which covers the spring insulator 4, is mounted on the proximal section of the housing 6. The wiring cover 7A is constituted by an inner circumferential cover 71, which is located on the inner circumferential side, and an outer circumferential cover 72, which overlaps the inner circumferential cover 71 on the outer circumferential side. The outer circumferential cover 72 includes introduction ports 721 through which air A is introduced. A filter 73 formed of a porous sheet is located between the inner circumferential cover 71 and the outer circumferential cover 72 in such a manner that the filter 73 covers the introduction ports 721. The filter 73 has properties that prevent liquid from passing through while permitting the passage of air.

A rubber bushing 74 through which lead wires 34 are inserted and retained is located on the inner circumferential side of the outer circumferential cover 72 to close the wiring cover 7A. The air A that is introduced into the wiring cover 7A through the introduction ports 721 and the filter 73 is introduced into the air duct 27 from the proximal end face of the sensor element 2.

An element cover 7B, which covers the distal end section of the sensor element 2, is mounted on the distal end section of the housing 6. Passage bores 75 are formed on the bottom and the side of the element cover 7B. The passage bores 75 introduce the exhaust gas G that passes through the pipe 8 of the exhaust system to the detector 205 of the sensor element 2 and allow the exhaust gas G to flow inside and outside the element cover 7B.

(Spring Insulator 4)

As shown in FIG. 1, the spring insulator 4 is also called as insulator glass and is formed of an insulating ceramic such as alumina. The spring insulator 4 is formed by compressing ceramic powder. The spring insulator 4 is located on top of the proximal section of the element insulator 5 in the insertion direction D and accommodates the proximal section 204 of the sensor element 2.

Figure 7:
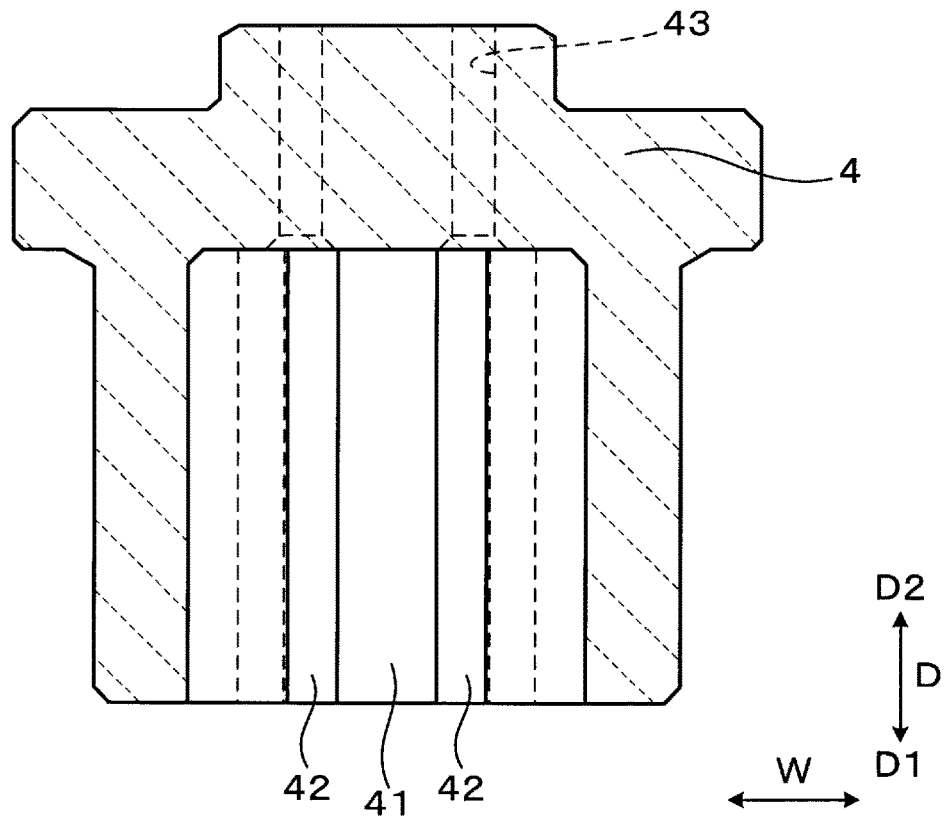
FIG. 7 is a cross-sectional view illustrating a spring insulator according to the first embodiment as viewed in the thickness direction of the sensor element.

As shown in FIGS. 2, 3 and 7, the insertion hole 41 of the spring insulator 4 is formed as a cavity having a closed end so as not to extend all through the spring insulator 4 from the distal end face in which the sensor element 2 is inserted. The insertion hole 41 is formed in a central position on a plane orthogonal to the insertion direction D. The insertion hole 41 is formed as a cavity having a substantially rectangular cross-section in conformance with the shape of the sensor element 2 having a substantially rectangular cross-section.

Figure 8:
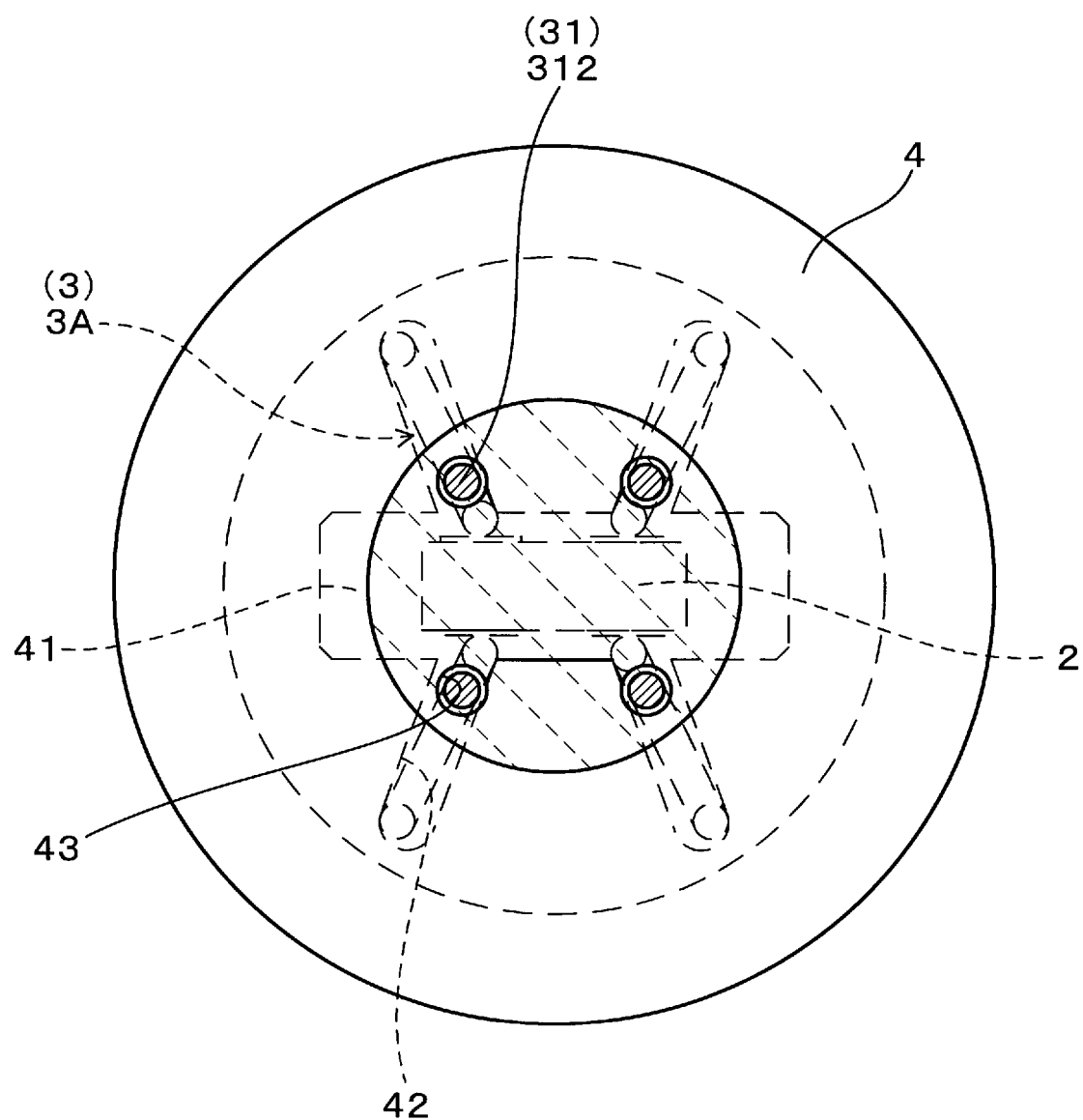
FIG. 8 is a cross-sectional view taken along line VIII-VIII of FIG. 1 as viewed from the direction of arrows illustrating the spring insulator and its surroundings according to the first embodiment.

As shown in FIGS. 2, 3, and 8, through holes 43 in which the ends of the holding sections 31 of the spring terminals 3 are inserted are formed in the proximal section of the spring insulator 4. The retaining grooves 42 of the spring insulator 4 are formed to extend from the distal end surface of the spring insulator 4 and communicate with the insertion hole 41 from the thickness direction T. The retaining grooves 42 are formed to incline with respect to the thickness direction T so that the inclined spring terminals 3A are arranged in an inclined state with respect to the thickness direction T. Part of the holding section 31 and part of the arm section 32 are located in the associated retaining groove 42 of the spring insulator 4. The outer circumferential surface of the spring insulator 4, which is the side surface parallel to the insertion direction D, has a circular cross-section. As shown in FIG. 7, the retaining grooves 42 are continuously formed from the distal end surface of the spring insulator 4 toward the proximal section.

(Spring Terminals 3)

Figure 9:
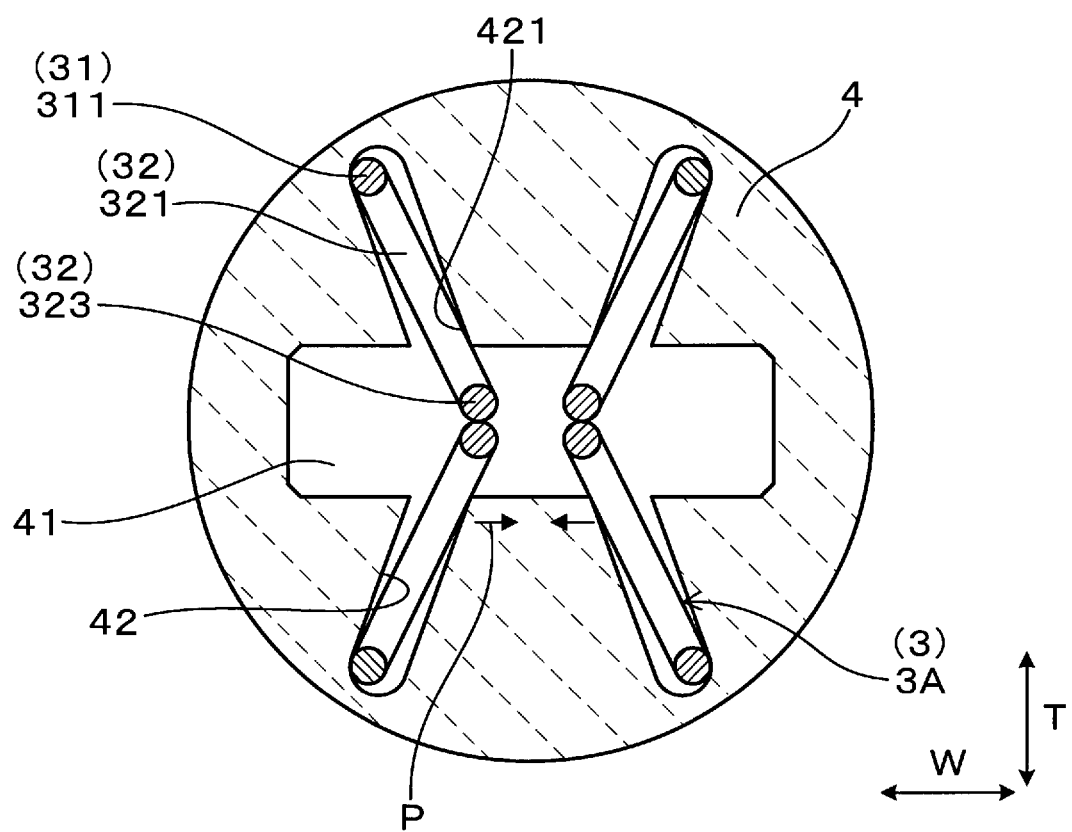
FIG. 9 is a cross-sectional view corresponding to the view taken along line III-III of FIG. 1 as viewed from the direction of arrows illustrating the spring insulator, which retains the spring terminals, according to the first embodiment before the sensor element is inserted.

As shown in FIGS. 2, 3, and 9, the spring insulator 4 retains the inclined spring terminals 3A the number of which is four. Each inclined spring terminal 3A comes into contact with the associated one of the two first terminal contact portions 28A and the two second terminal contact portions 28B individually. The arm section 32 of each inclined spring terminal 3A is folded back from the holding section 31 and faces the holding section 31 in the flexing direction F. Since the arm section 32 is formed to face the holding section 31, the spring properties of the arm section 32 in which the arm section 32 flexes (elastically deforms) with respect to the holding section 31 are easily exhibited. The flexing direction F of the arm section 32 of the present embodiment is a direction in which the holding section 31 and the arm section 32 face each other.

As shown in FIG. 2, each holding section 31 includes a main body section 311, which is located on the outer circumferential end of the associated retaining groove 42, an extended section 312, which is inserted in the associated through hole 43, and a joint section 313, which connects the main body section 311 and the extended section 312 with each other. The main body section 311 and the extended section 312 are formed to be offset in a direction orthogonal to the insertion direction D while being parallel to each other. The arm section 32 includes a curved section 321, which is connected to the main body section 311 of the holding section 31, a straight section 322, which is connected to the curved section 321, a contact section 323, which is formed on the straight section 322 and comes into contact with the associated one of the terminal contact portions 28A and 28B. The contact section 323 is curved.

When mainly the curved section 321 is elastically deformed to reduce the radius of curvature, the straight section 322 and the contact section 323 of each arm section 32 flex to approach the main body section 311 of the holding section 31. The arm section 32 also flexes as the entire arm section 32 except the curved section 321 warps. When the arm sections 32 flex by contacting the terminal contact portions 28A and 28B, the spring restoration force of the arm sections 32 that causes the arm sections 32 to restore to the original state acts on the terminal contact portions 28A and 28B.

As shown in FIGS. 1 and 2, terminal metal fittings 33 are fitted to the extended sections 312 of the holding sections 31 of the spring terminals 3, which are inserted in the through holes 43 of the spring insulator 4, from the proximal end of the spring insulator 4. The lead wires 34, which are connected to, for example, a controller outside the gas sensor 1, are attached to the terminal metal fittings 33.

The spring terminals 3 of the present embodiment are formed of a round wire (steel wire) having a circular cross-section with a wire diameter in the range of φ 0.4 to 0.7 mm. The holding sections 31 and the arm sections 32 are formed by bending the round wire. The width of the wire forming the spring terminals 3 is minimized by using the round wire while ensuring the strength. Using the round wire reduces the space occupied by the spring terminals 3 in the spring insulator 4. This reduces the size of the spring insulator 4 and thus the size of the gas sensor 1.

If the wire diameter of the spring terminals 3 is less than φ 0.4 mm, as shown in FIG. 3, a gap S between each spring terminal 3 and the associated retaining groove 42 of the spring insulator 4 in which the spring terminal 3 is located is increased. Thus, the positional displacement amount of the spring terminal 3 in the associated retaining groove 42 in the widthwise direction W is increased. This necessitates the increase in the width of the terminal contact portions 28A and 28B on the sensor element 2 in the widthwise direction W, which becomes a factor in hindering the size reduction of the sensor element 2.

If the wire diameter of the spring terminals 3 exceeds φ 0.7 mm, the arm sections 32 of the spring terminals 3 become less flexible. This becomes a factor in deteriorating the ease of inserting the sensor element 2 in the insertion hole 41 of the spring insulator 4 in which the spring terminals 3 are retained. Additionally, in view of ensuring the strength of a mold for forming the spring insulator 4, the width of the retaining grooves 42 of the spring insulator 4 in which the spring terminals 3 are located is preferably 0.7 mm or more.

Note that, the cross-sectional shape of the spring terminals 3 may be a flat shape, an elliptic shape, and an angular shape including a rectangular shape. In this case, the aspect ratio of the cross-section of the spring terminals 3 may be in the range of 1:1 to 1:2. The aspect ratio is the ratio of the length of the major axis (long side) to the length of the minor axis (short side).

As shown in FIG. 3, the inclined spring terminals 3A are located side by side in the widthwise direction W and are also located to face each other with the sensor element 2 located in between. The inclined spring terminals 3A are located on both sides of the sensor element 2 in the thickness direction T in a pair to be side by side in the widthwise direction W. Two of the inclined spring terminals 3A are located side by side in the widthwise direction W to face the first outer surface 201 corresponding to the two first terminal contact portions 28A on the first outer surface 201 at the proximal section 204 of the sensor element 2. Additionally, two of the inclined spring terminals 3A are located side by side in the widthwise direction W to face the second outer surface 202 corresponding to the two second terminal contact portions 28B on the second outer surface 202 at the proximal section 204 of the sensor element 2. The two inclined spring terminals 3A located to face the first outer surface 201 and the two inclined spring terminals 3A located to face the second outer surface 202 face each other with the sensor element 2 located in between.

Additionally, the direction in which the inclined spring terminals 3A are inclined is such that the arm sections 32 are located closer to the center than the holding sections 31 are in the widthwise direction W of the sensor element 2. When the spring insulator 4 is viewed in the insertion direction D, the four inclined spring terminals 3A are arranged to be inclined with respect to the thickness direction T of the sensor element 2 in such a manner that resembles the shape of a letter X.

Since the inclined spring terminals 3A face one another with the sensor element 2 located in between, as shown in FIG. 9, when the sensor element 2 is not inserted in the insertion hole 41 of the spring insulator 4, the contact sections 323 of the arm sections 32 of the inclined spring terminals 3A that face each other in the thickness direction T come into contact with each other. In this state, since the arm sections 32 are located closer to the center than the holding sections 31 in the widthwise direction W of the sensor element 2, the contact sections 323 of the arm sections 32 of the inclined spring terminals 3A that face each other are displaced toward the center in the widthwise direction W. Thus, the arm sections 32 of the inclined spring terminals 3A are prevented from being displaced in different directions of the widthwise direction W from each other. Additionally, the contact sections 323 of the arm sections 32 are prevented from being displaced from the terminal contact portions 28A and 28B outward in the widthwise direction W and going out of the sensor element 2 in the widthwise direction W. In the drawing, the directions in which the contact sections 323 of the arm sections 32 are displaced are shown by arrows P.

Since the arm sections 32 of the inclined spring terminals 3A are located closer to the center than the holding sections 31 in the widthwise direction W of the sensor element 2, the inclined spring terminals 3A are arranged as close as possible to a radial pattern in the spring insulator 4. Thus, the gap between the holding sections 31 of the pair of inclined spring terminals 3A located side by side in the widthwise direction W is widened. Consequently, the interference between the terminal metal fittings 33, which are connected to the inclined spring terminals 3A, and between the lead wires 34, which are connected to the inclined spring terminals 3A through the terminal metal fittings 33, is easily avoided.

As shown in FIG. 3, the arm sections 32 of the inclined spring terminals 3A in contact with the terminal contact portions 28A and 28B of the sensor element 2 are flexed with the inclination angle θ of a central axis O along the flexing direction F with respect to a normal M perpendicular to the outer surfaces of the terminal contact portions 28A and 28B being increased compared with a state before coming into contact with the terminal contact portions 28A and 28B. The central axis O refers to an imaginary line that passes through the center of the cross-section of the arm section 32 when viewed from the insertion direction D. In this state, the arm section 32 of each inclined spring terminal 3A is in contact with a side surface 421 of the associated retaining groove 42 closer to the center in the widthwise direction W, so that the position relative to the outer surface of the associated one of the terminal contact portions 28A and 28B is fixed.

As shown in the drawing, the width of the retaining grooves 42 of the spring insulator 4 is greater than the wire diameter of the spring terminals 3. The gap S is formed between each retaining groove 42 and the associated spring terminal 3. Thus, when the arm sections 32 of the inclined spring terminals 3A come into contact with the terminal contact portions 28A and 28B, each arm section 32 is displaced within the range of the gap S. At this time, since the flexing direction F of the inclined spring terminals 3A is inclined with respect to the outer surfaces of the terminal contact portions 28A and 28B, the direction in which the arm section 32 of each inclined spring terminal 3A is displaced is the direction in which the inclination angle θ of the central axis O of the arm section 32 with respect to the normal M is increased.

When each arm section 32 comes into contact with the side surface 421 of the associated retaining groove 42 closer to the center in the widthwise direction W, the displacement of the arm section 32 in the widthwise direction W is restricted. In this manner, the position of the arm sections 32 with respect to the outer surfaces of the terminal contact portions 28A and 28B is fixed. Thus, the position of the arm sections 32 in the widthwise direction W with respect to the outer surfaces of the terminal contact portions 28A and 28B is stabilized. Consequently, the contact state of the inclined spring terminals 3A with respect to the terminal contact portions 28A and 28B is reliably maintained.

When the sensor element 2 and the inclined spring terminals 3A, which are retained by the spring insulator 4, are viewed in the insertion direction D, the inclination angle θ between the central axis O along the flexing direction F of the inclined spring terminal 3A and the normal M perpendicular to the outer surfaces of the terminal contact portions 28A and 28B is within the range of 5 to 45°. If the inclination angle θ is less than 5°, it is difficult to achieve the advantage obtained by tilting the flexing direction F of the arm sections 32 of the inclined spring terminals 3A with respect to the outer surfaces of the terminal contact portions 28A and 28B. If the inclination angle θ exceeds 45°, the arm sections 32 of the inclined spring terminals 3A easily slide along the outer surfaces of the terminal contact portions 28A and 28B, so that the contact state between the inclined spring terminals 3A and the terminal contact portions 28A and 28B may possibly deteriorate.

As shown in FIG. 9, the two inclined spring terminals 3A located side by side in the widthwise direction W are arranged at positions and with inclination angles such that when the sensor element 2 is not inserted in the insertion hole 41 of the spring insulator 4, the arm sections 32 of the two inclined spring terminals 3A located side by side in the widthwise direction W do not come into contact with each other. If the arm sections 32 of the two inclined spring terminals 3A located side by side in the widthwise direction W come into contact with each other, the ease of inserting the sensor element 2 in the insertion hole 41 deteriorates. In this case, it is difficult to provide the terminal contact portions 28A and 28B located side by side in the widthwise direction W on the outer surfaces 201 and 202 of the sensor element 2.

Subsequently, the operational effects of the gas sensor 1 according to the present embodiment will be described.

In order to use the spring terminals 3 formed of a round wire, the gas sensor 1 of the present embodiment is designed to reliably maintain the contact state of the spring terminals 3 with respect to the terminal contact portions 28A and 28B on the outer surfaces 201 and 202 of the sensor element 2. More specifically, the spring restoration force that acts on the arm sections 32 of the spring terminals 3 is made to act on the outer surfaces of the terminal contact portions 28A and 28B in a state inclined with respect to the thickness direction T. Thus, the contact sections 323 of the arm sections 32 are allowed to be displaced only toward the center in the widthwise direction W of the outer surfaces of the terminal contact portions 28A and 28B.

(State before Insertion of Element)

Figure 10:
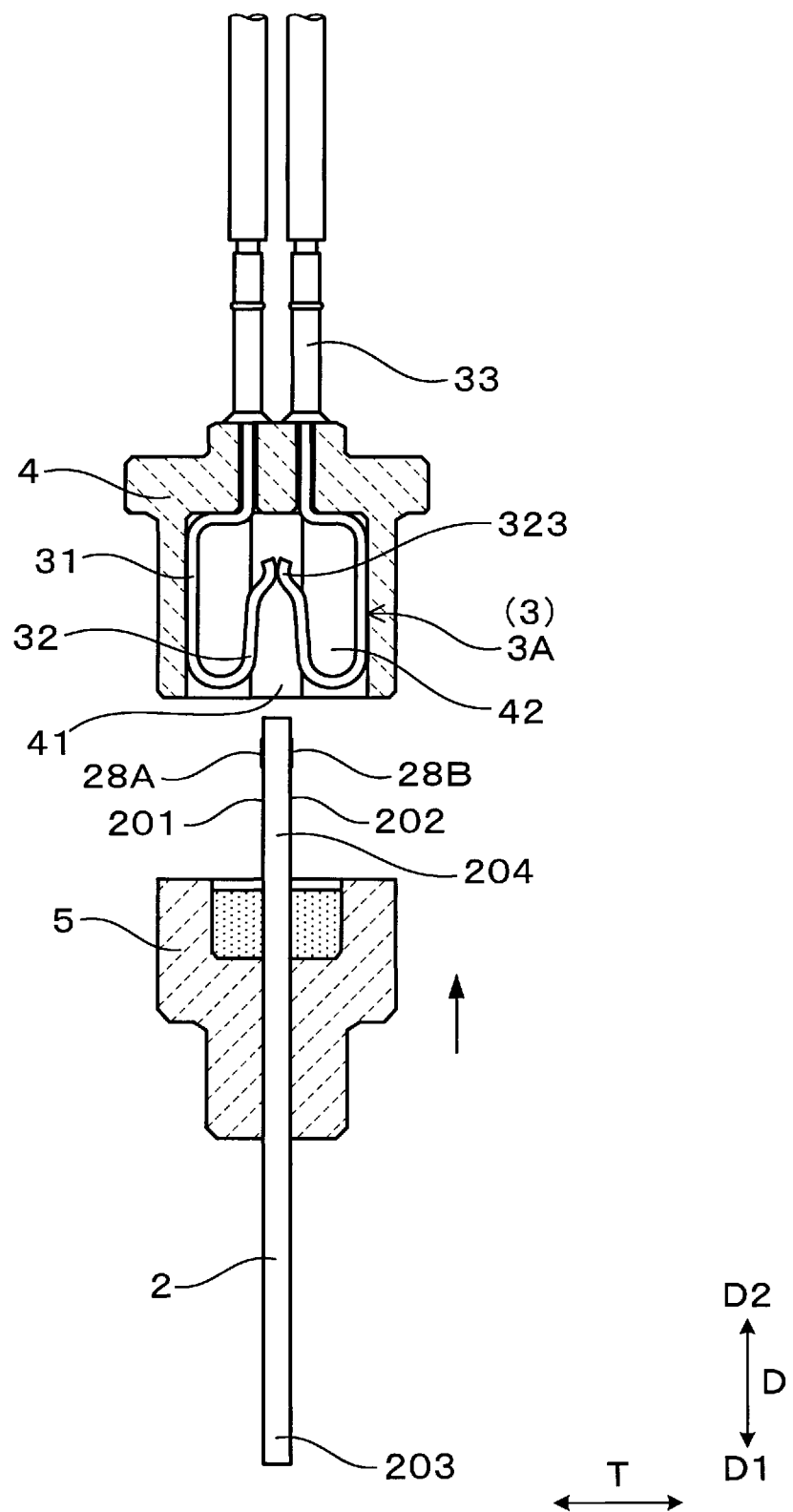
FIG. 10 is a cross-sectional view illustrating a state in which the sensor element is about to be inserted in the insertion hole of the spring insulator, which retains the spring terminals, according to the first embodiment.

As shown in FIG. 9, in a state before the insertion of the element, in which the proximal section 204 of the sensor element 2 is not inserted in the insertion hole 41 of the spring insulator 4, the arm sections 32 of the inclined spring terminals 3A are in contact with each other in the thickness direction T while applying the spring restoration force in a direction inclined with respect to the thickness direction T. At this time, the positions of both the arm sections 32 of the inclined spring terminals 3A that are in contact with each other are determined at positions displaced toward the center in the widthwise direction W by the action of the spring restoration force. Thus, the arm sections 32 that are in contact with each other are prevented from being displaced in different directions from each other in the widthwise direction W, and the arm sections 32 that are in contact with each other are prevented from passing by each other in the widthwise direction W. Thus, as shown in FIG. 10, when the proximal section 204 of the sensor element 2 is inserted in the insertion hole 41 of the spring insulator 4, the arm sections 32 are smoothly flexed, so that the ease of inserting the sensor element 2 in the insertion hole 41 is reliably maintained.

Figure 11:
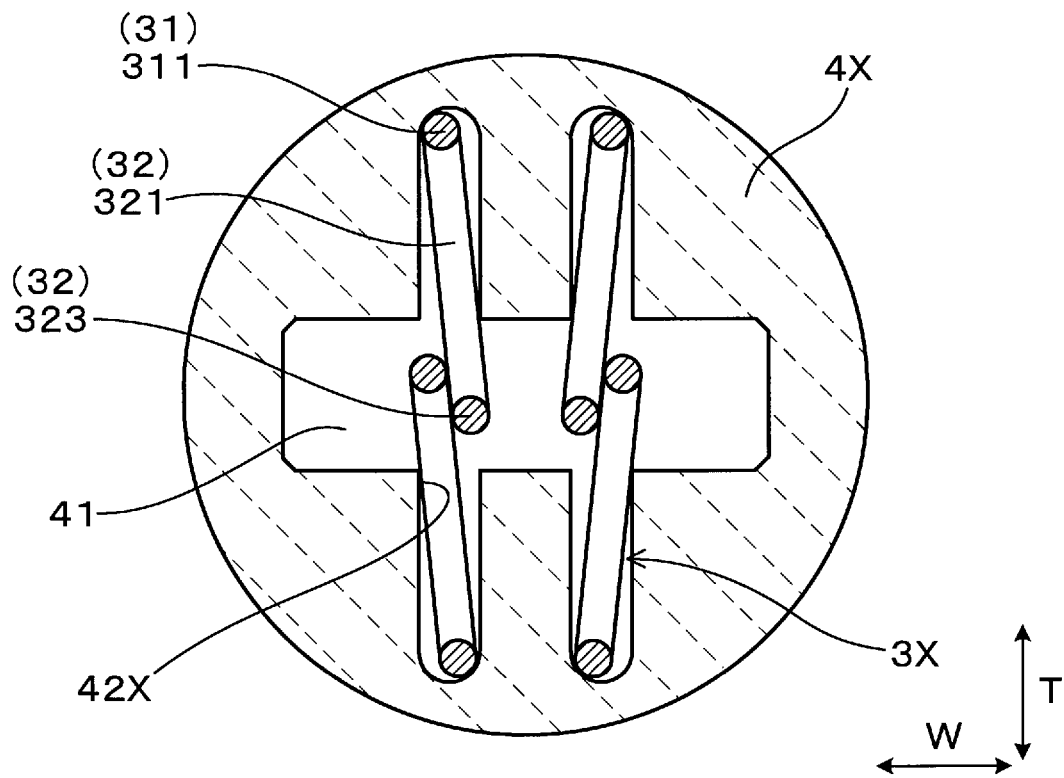
FIG. 11 is a cross-sectional view corresponding to the view taken along line III-III of FIG. 1 as viewed from the direction of arrows illustrating a spring insulator, which retains spring terminals, according to a comparative embodiment before a sensor element is inserted.

As a comparative embodiment, as shown in FIG. 11, if the arm sections 32 of spring terminals 3X that are in contact with each other in the thickness direction T cause the spring restoration force to act in the thickness direction T, since the spring terminals 3X are formed of a round wire, the arm sections 32 may possibly be displaced in different directions from each other in the widthwise direction W and pass by each other in the widthwise direction W. In the drawing, the spring insulator is denoted by the reference signs 4X, and the retaining grooves are denoted by the reference signs 42X. In this case, when the proximal section 204 of the sensor element 2 is inserted in the insertion hole 41 of the spring insulator 4X, the arm sections 32 may possibly fail to smoothly flex, so that the ease of inserting the sensor element 2 in the insertion hole 41 may possibly deteriorate.
(State after Insertion of Element)

As shown in FIG. 3, in the state after the insertion of the element, in which the proximal section 204 of the sensor element 2 is inserted in the insertion hole 41 of the spring insulator 4, the contact sections 323 of the arm sections 32 of the inclined spring terminals 3A are displaced only toward the center in the widthwise direction W with respect to the outer surfaces of the terminal contact portions 28A and 28B. The arm sections 32 are displaced in such a manner that the inclination angle $\theta$ between the central axis O of each arm section 32 and the normal M is increased. In the drawing, the directions in which the contact sections 323 of the arm sections 32 are displaced are shown by arrows P.

The arm section 32 of each inclined spring terminal 3A comes into contact with the side surface 421 of the associated retaining groove 42 of the spring insulator 4 closer to the center in the widthwise direction W. Thus, the direction in which the contact sections 323 of the arm sections 32 are displaced and the amount of the displacement are restricted, so that the positions where the contact sections 323 of the arm sections 32 come into contact with the outer surfaces of the terminal contact portions 28A and 28B are determined. Since the contact positions of the arm sections 32 with respect to the terminal contact portions 28A and 28B are determined, contact failure between the arm sections 32 and the terminal contact portions 28A and 28B is unlikely to occur.

Figure 12:
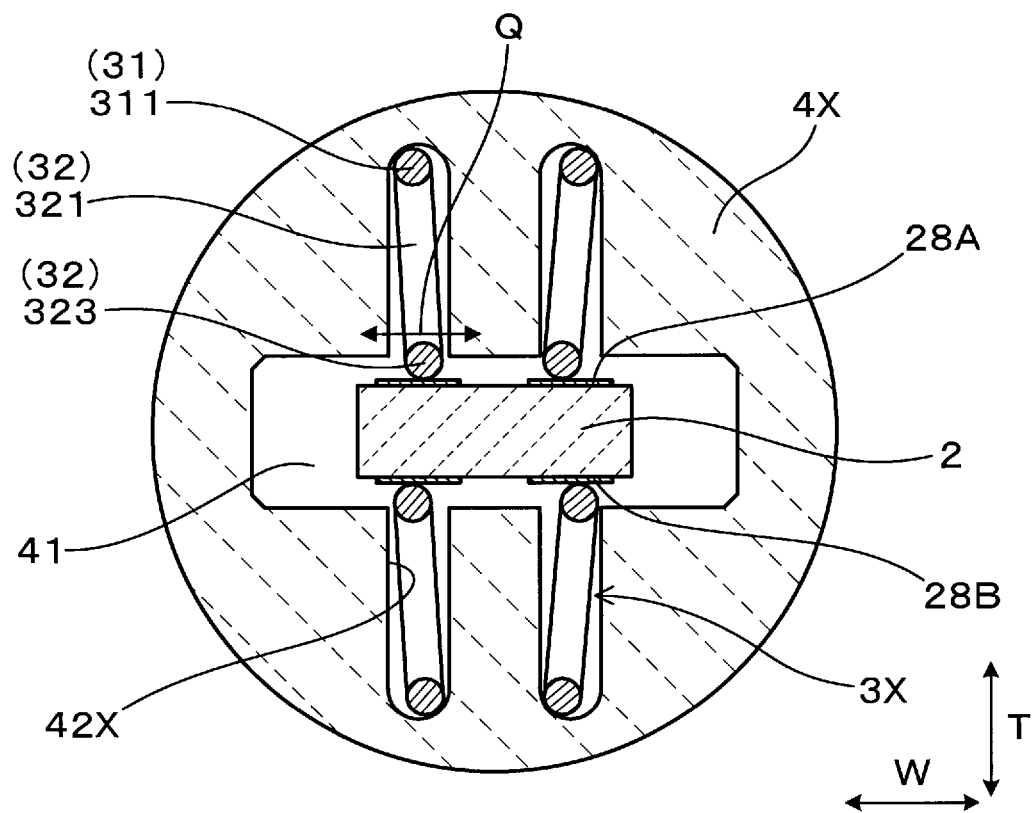
FIG. 12 is a cross-sectional view corresponding to the view taken along line III-III of FIG. 1 as viewed from the direction of arrows illustrating a state in which the sensor element is inserted in an insertion hole of the spring insulator, which retains the spring terminals, according to the comparative embodiment.

As a comparative embodiment, as shown in FIG. 12, if the arm sections 32 of the spring terminals 3X that are in contact with each other in the thickness direction T cause the spring restoration force to act in the thickness direction T, the side in the widthwise direction W to which the arm sections 32 will be displaced is apt to change. In the drawing, the state where the direction in which the contact sections 323 of the arm sections 32 will be displaced is apt to change is indicated by the reference sign Q. This causes variation in the positions where the contact sections 323 of the arm sections 32 come into contact with the outer surfaces of the terminal contact portions 28A and 28B. Consequently, the contact positions of the arm sections 32 with respect to the terminal contact portions 28A and 28B are apt to change, and contact failure may possibly occur between the arm sections 32 and the terminal contact portions 28A and 28B.

In this manner, with the gas sensor 1 having the contact structure of the inclined spring terminals 3A according to the present embodiment, the state of the inclined spring terminals 3A is maintained in an appropriate manner either before or after the insertion of the sensor element 2 to the insertion hole 41 of the spring insulator 4. Consequently, according to the gas sensor 1 of the present embodiment, the state of the electrical connection between the spring terminals 3 and the sensor element 2 is made favorable.

Figure 13:
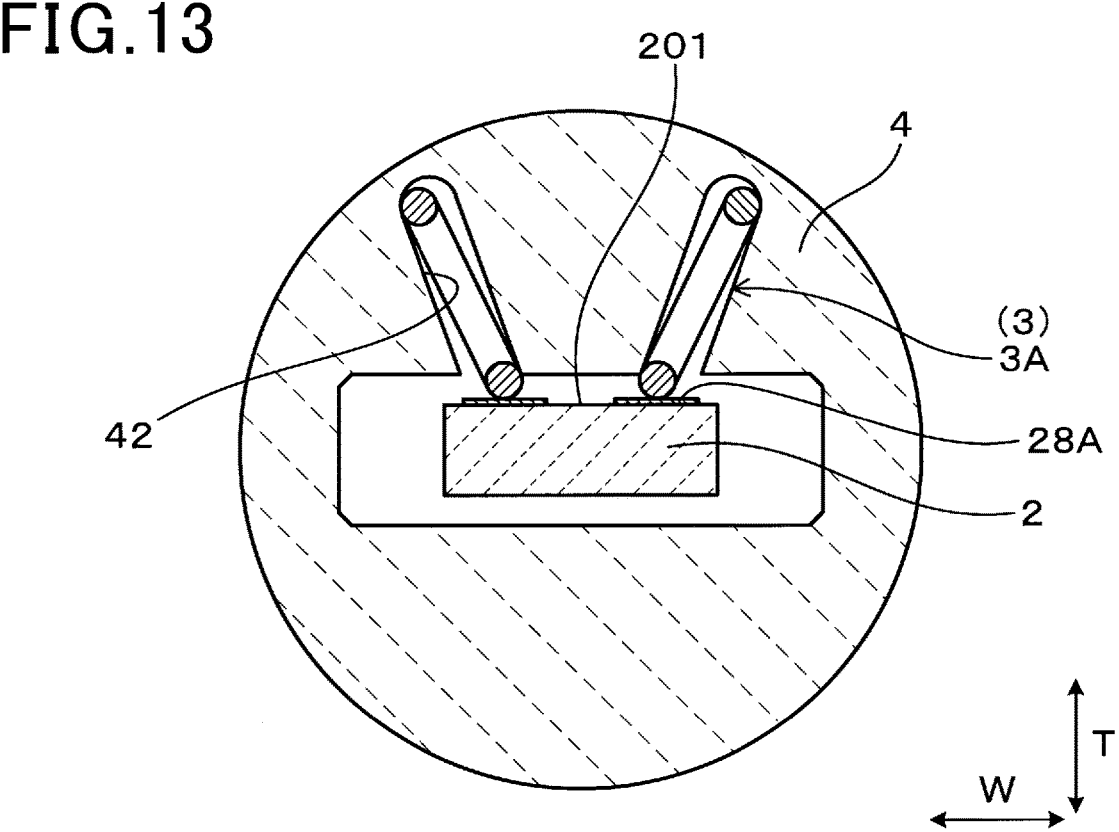
FIG. 13 is a cross-sectional view corresponding to the view taken along line III-III of FIG. 1 as viewed from the direction of arrows illustrating spring terminals of another gas sensor and their surroundings according to the first embodiment.

When the heater 23 is not laminated on the sensor element 2, the second terminal contact portions 28B and the inclined spring terminals 3A, which are in contact with the second terminal contact portions 28B, are unnecessary. In this case, as shown in FIG. 13, the first terminal contact portions 28A may be formed on the first outer surface 201 of the sensor element 2, and only the two inclined spring terminals 3A that come into contact with the first terminal contact portions 28A on the first outer surface 201 of the sensor element 2 may be provided.

Second Embodiment

The present embodiment illustrates a case in which the number of the spring terminals 3 in the spring insulator 4 is six.

Figure 14:
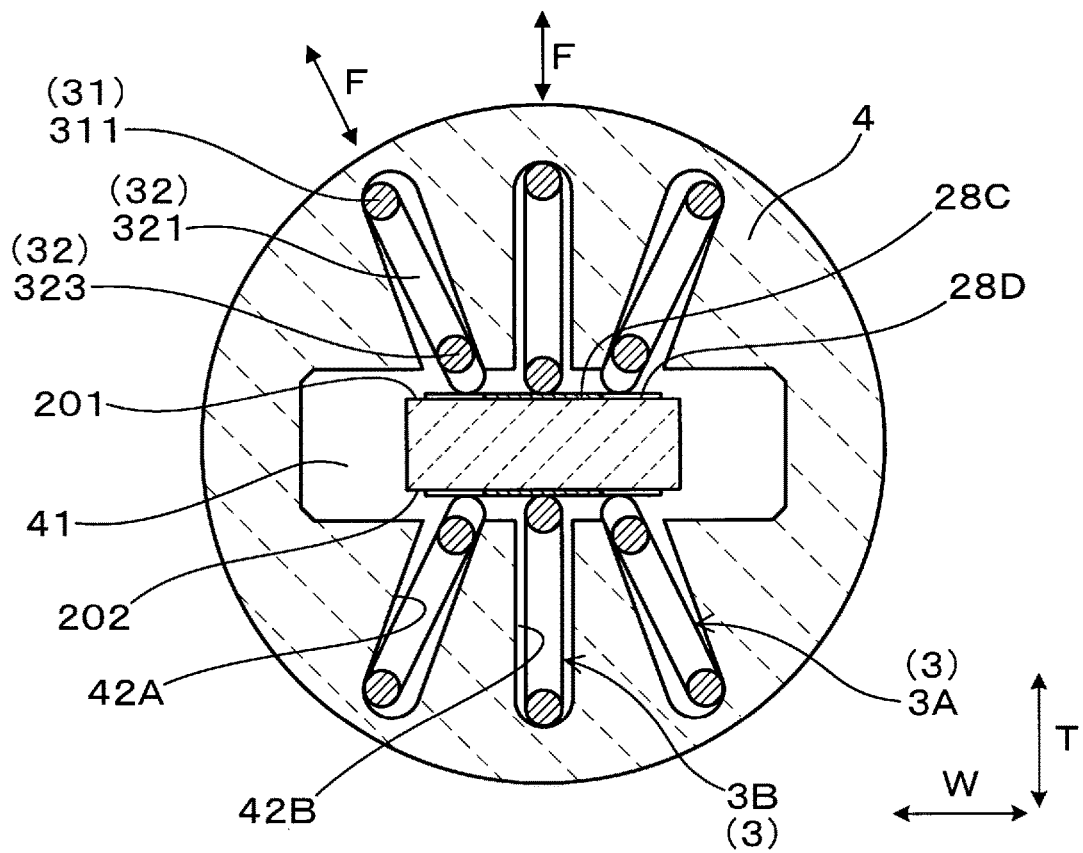
FIG. 14 is a cross-sectional view corresponding to the view taken along line III-III of FIG. 1 as viewed from the direction of arrows illustrating spring terminals of a gas sensor and their surroundings according to a second embodiment.

As shown in FIG. 14, the spring insulator 4 of the present embodiment retains two vertical spring terminals 3B besides the four inclined spring terminals 3A. The vertical spring terminals 3B are the spring terminals 3 other than the inclined spring terminals 3A among the multiple spring terminals 3, which are retained by the spring insulator 4.

The vertical spring terminals 3B are each located between the pair of inclined spring terminals 3A, which are located side by side in the widthwise direction W, in such a manner that the flexing direction F of the arm section 32 is perpendicular to the outer surfaces of the terminal contact portions 28A and 28B. The spring insulator 4 includes retaining grooves 42A for the inclined spring terminals 3A, which are inclined with respect to the thickness direction T, and retaining grooves 42B for the vertical spring terminals 3B, which are parallel to the thickness direction T.

The number of the spring terminals 3 used in the present embodiment is six in total since the number of the electrodes located on the sensor element 2 is four, and the number of the lead portions 232 of the heating element 230 of the heater 23 is two. The gas sensor 1 of the present embodiment may be, for example, a NOx sensor, which detects the concentration of a specific gas component such as NOx (nitrogen oxide). The sensor element 2 of the NOx sensor uses four electrodes including a pumping electrode, which is located on the first main surface 211 of the solid electrolyte 21 for discharging oxygen in the exhaust gas G in the gas chamber 26, a monitor electrode, which is located on the first main surface 211 of the solid electrolyte 21 for detecting the residual oxygen concentration in the exhaust gas G in the gas chamber 26, a sensor electrode, which is located on the first main surface 211 of the solid electrolyte 21 for detecting the NOx concentration in the exhaust gas G in the gas chamber 26, and a reference electrode, which is located on the second main surface 212 of the solid electrolyte 21 and is exposed to the air A. Additionally, the heater 23 is laminated on the sensor element 2.

Figure 15:
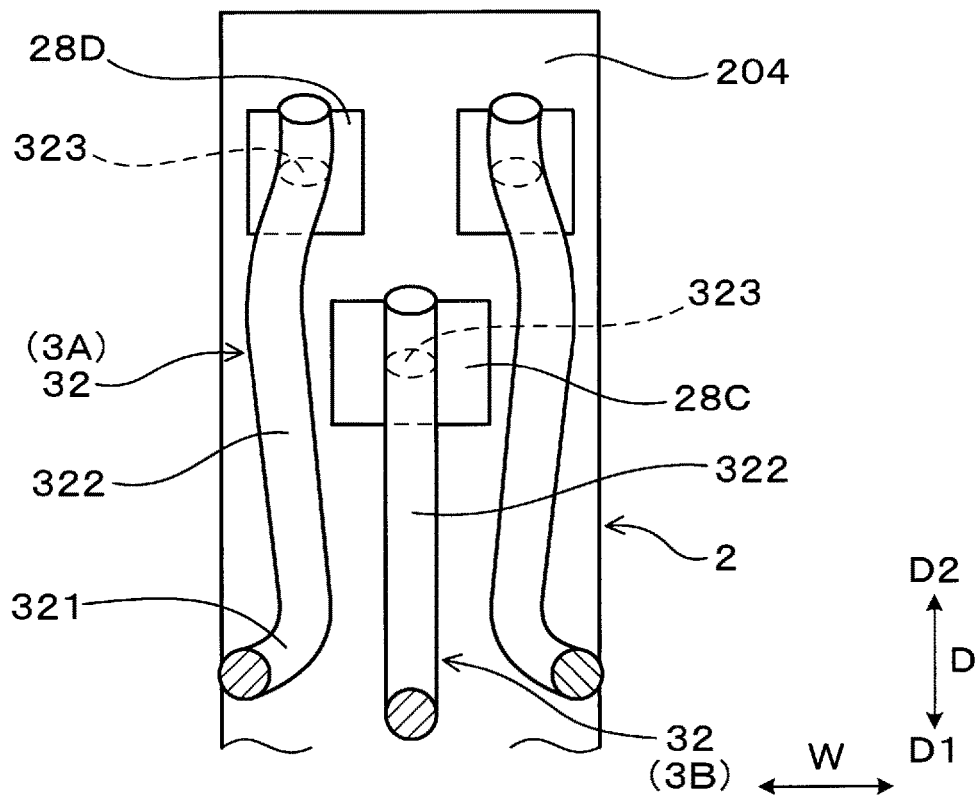
FIG. 15 is an explanatory diagram illustrating terminal contact portions on an outer surface of a sensor element and their surroundings according to the second embodiment as viewed in the thickness direction of the sensor element.

As shown in FIG. 15, the first outer surface 201 and the second outer surface 202 of the sensor element 2 each include three terminal contact portions 28C and 28D. The first outer surface 201 includes three terminal contact portions 28C and 28D that are connected to the lead portions 221 of the pumping electrode, the monitor electrode, and the sensor electrode. The second outer surface 202 includes three terminal contact portions 28C and 28D that are connected to the lead portion 221 of the reference electrode and the lead portions 232 of the heating element 230 of the heater 23.

The three terminal contact portions 28C and 28D, which are formed on each of the outer surfaces 201 and 202 of the sensor element 2, include two proximal terminal contact portions 28D and a distal terminal contact portion 28C. The proximal terminal contact portions 28D are located side by side in the widthwise direction W on the proximal end of the proximal section 204 of the sensor element 2. The distal terminal contact portion 28C is formed adjacent to the distal ends of the proximal terminal contact portions 28D. The arm sections 32 of the two inclined spring terminals 3A that are located side by side in the widthwise direction W come into contact with the two proximal terminal contact portions 28D. The arm section 32 of each vertical spring terminal 3B is in contact with the associated distal terminal contact portion 28C.

As shown in FIG. 15, the formation width in the widthwise direction W of the distal terminal contact portion 28C, which is in contact with the vertical spring terminal 3B, is greater than the formation width of the proximal terminal contact portions 28D in the widthwise direction W. Thus, the displacement of the arm section 32 of each vertical spring terminal 3B to either side of the sensor element 2 in the widthwise direction W is allowable. The correspondence of the pumping electrode, the monitor electrode, the sensor electrode, the reference electrode, and the heating element 230 with respect to the inclined spring terminals 3A and the vertical spring terminals 3B may be changed.

In the gas sensor 1 of the present embodiment, the vertical spring terminal 3B is located between each pair of the inclined spring terminals 3A in response to the increase in the number of the electrodes used for the sensor element 2. The formation width in the widthwise direction W of the distal terminal contact portion 28C with which the vertical spring terminal 3B is in contact is greater than the formation width in the widthwise direction W of the proximal terminal contact portions 28D with which the inclined spring terminals 3A are in contact. Thus, even if the vertical spring terminals 3B are used, the contact state between the vertical spring terminals 3B and the distal terminal contact portions 28C is reliably maintained.

When the heater 23 is not laminated on the sensor element 2 of the NOx sensor, four electrodes including the pumping electrode, the monitor electrode, the sensor electrode, and the reference electrode may correspond to the two terminal contact portions 28A and the two terminal contact portions 28B formed on the first outer surface 201 of the sensor element 2 or on the second outer surface 202 of the sensor element 2, and the four inclined spring terminals 3A.

Figure 16:
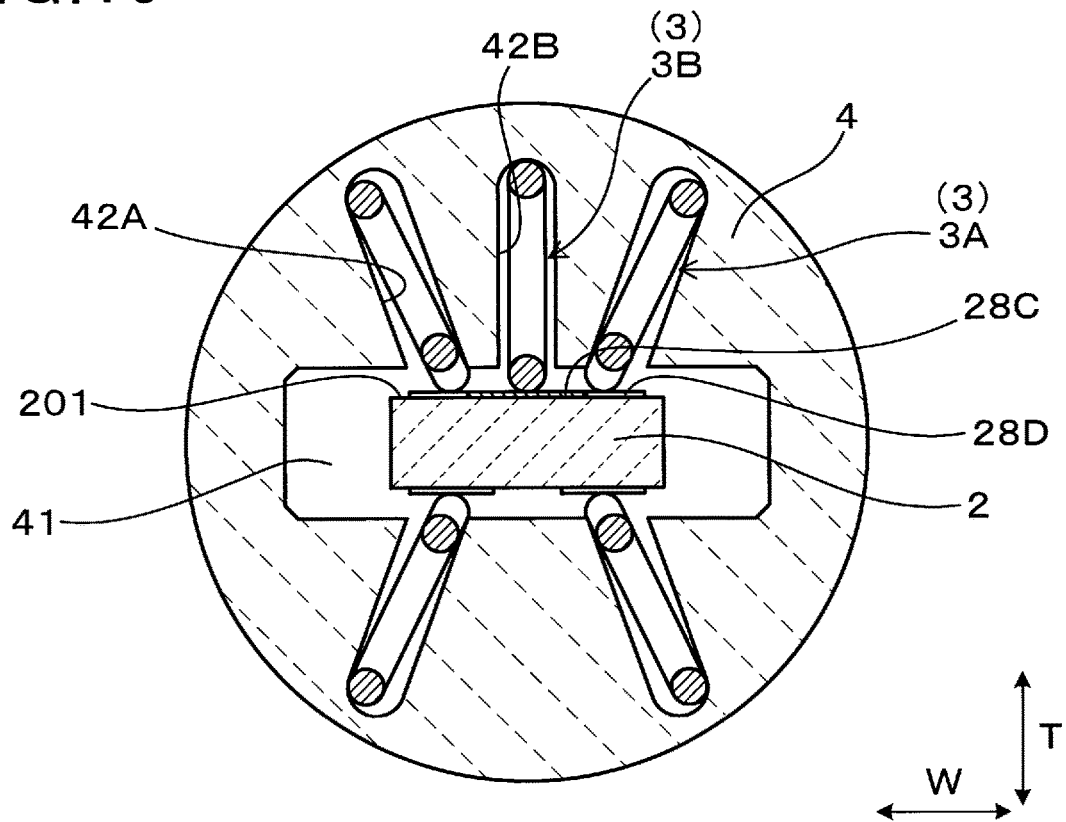
FIG. 16 is a cross-sectional view corresponding to the view taken along line III-III of FIG. 1 as viewed from the direction of arrows illustrating spring terminals of another gas sensor and their surroundings according to the second embodiment.

Alternatively, as shown in FIG. 16, the vertical spring terminal 3B may be used only on the first outer surface 201 of the sensor element 2, so that the gas sensor 1 uses a total of five spring terminals 3.

Other structures and the operational effects of the gas sensor 1 of the present embodiment are the same as those of the first embodiment. In the present embodiment also, the components indicated by the same reference numerals as the reference numerals indicated in the first embodiment are the same as those in the first embodiment.

Third Embodiment

The present embodiment illustrates a modification of the retaining grooves 42 of the spring insulator 4.

Figure 17:
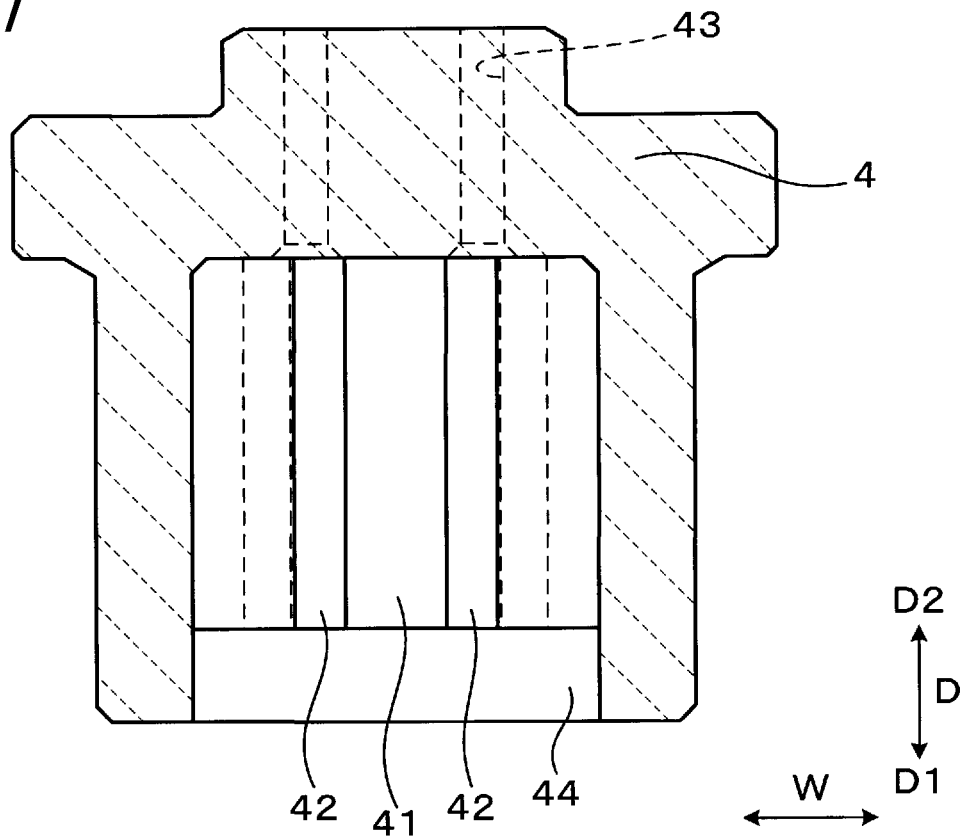
FIG. 17 is a cross-sectional view illustrating how retaining grooves of a spring insulator according to a third embodiment are formed as viewed in the thickness direction of a sensor element.

As shown in FIG. 17, the retaining grooves 42 do not necessarily have to be formed continuously from the distal end surface toward the proximal end of the spring insulator 4, but may be formed from a recess 44, which is formed at the distal end section of the spring insulator 4, toward the proximal end.

Figure 18:
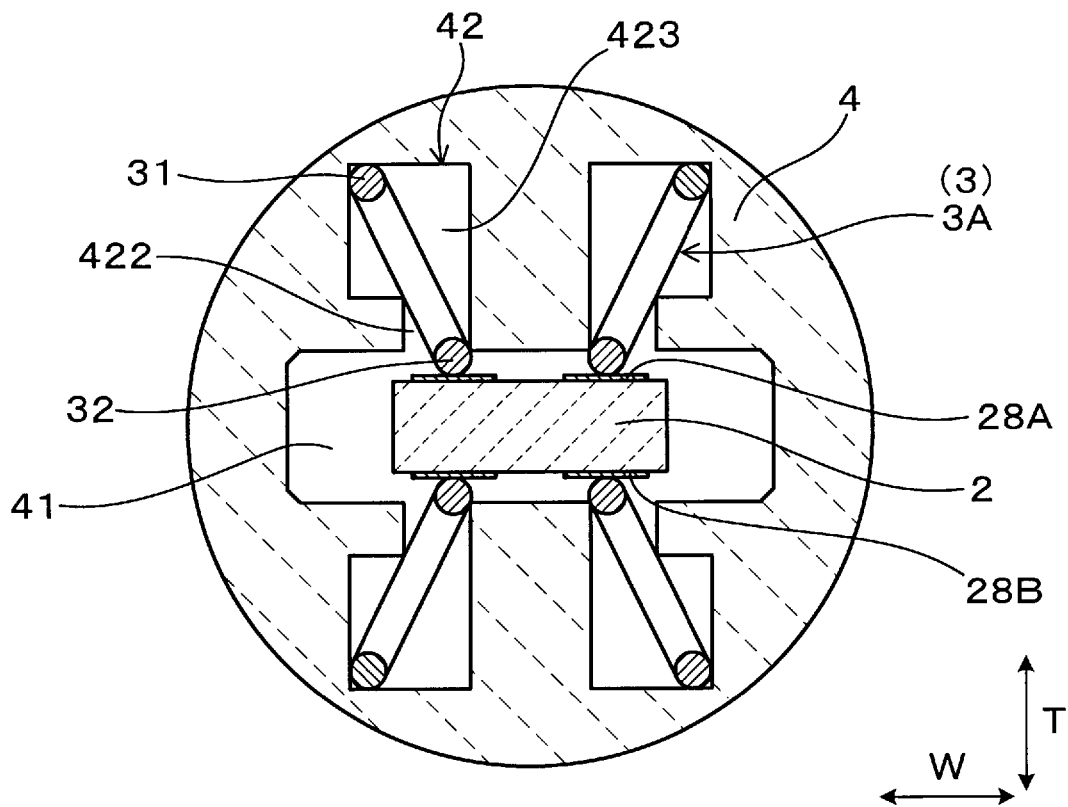
FIG. 18 is a cross-sectional view corresponding to the view taken along line III-III of FIG. 1 as viewed from the direction of arrows illustrating how retaining grooves of the spring insulator according to the third embodiment are formed.
Figure 19:
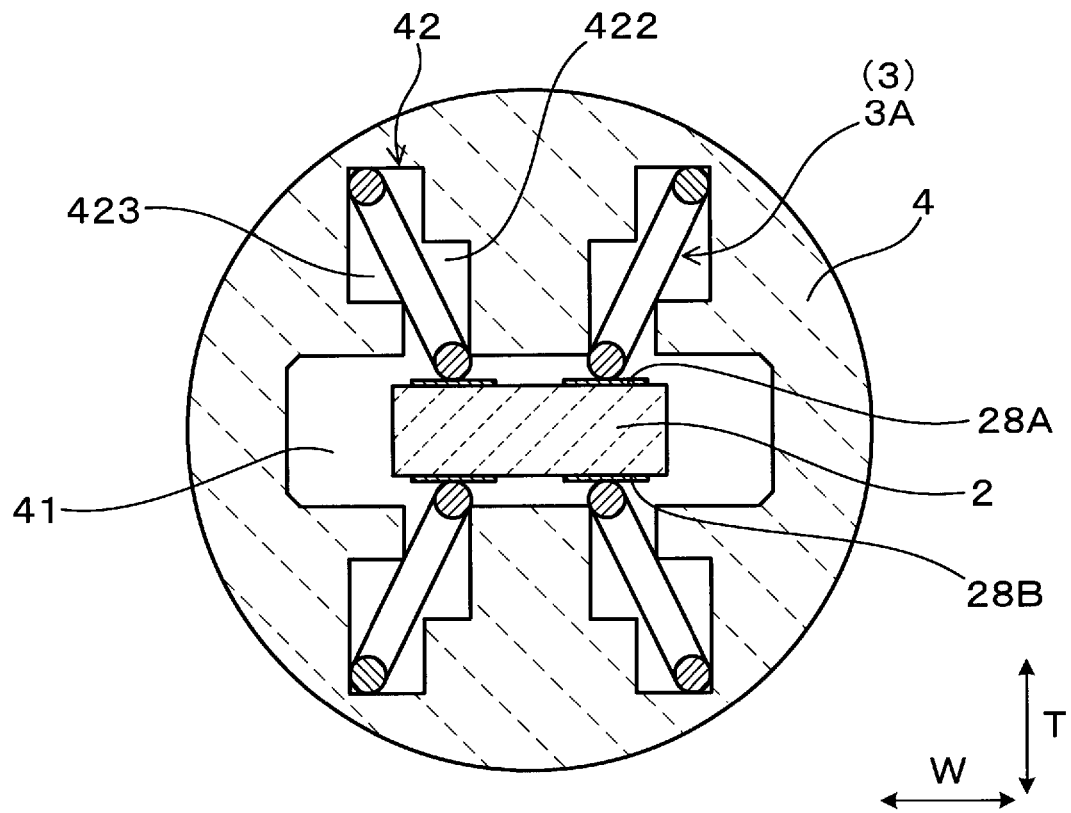
FIG. 19 is a cross-sectional view corresponding to the view taken along line III-III of FIG. 1 as viewed from the direction of arrows illustrating how retaining grooves of another spring insulator according to the third embodiment are formed.

Alternatively, besides forming the retaining grooves 42 to be straight as viewed from the insertion direction D, as shown in FIGS. 18 and 19, the retaining grooves 42 may be step-shaped as viewed from the insertion direction D. The step-shaped retaining grooves 42 are formed so that the inclined spring terminals 3A are arranged to be inclined with respect to the thickness direction T of the sensor element 2. The holding section 31 of each inclined spring terminal 3A is located at the outer corner in the associated step-shaped retaining groove 42 in the widthwise direction W. The arm section 32 of each inclined spring terminal 3A is located toward the center from the holding section 31 in the widthwise direction W.

FIG. 18 shows an example in which the width in the widthwise direction W of a section 422 of each retaining groove 42 located closer to the center in the thickness direction T is smaller than the width in the widthwise direction W of a section 423 of the retaining groove 42 located outward in the thickness direction T. Alternatively, FIG. 19 shows an example in which the section 422 of each retaining groove 42 located closer the center in the thickness direction T is formed closer to the center in the widthwise direction W than the section 423 of the retaining groove 42 located outward in the thickness direction T. The formation of the step-shaped retaining grooves 42 allows the inclined spring terminals 3A to be inclined with respect to the outer surfaces of the terminal contact portions 28A and 28B.

Other structures and the operational effects of the gas sensor 1 of the present embodiment are the same as those of the first embodiment. In the present embodiment also, the components indicated by the same reference numerals as the reference numerals indicated in the first embodiment are the same as those in the first embodiment.

Fourth Embodiment

The present embodiment illustrates a modification of the shape of the spring terminals 3.

Figure 20:
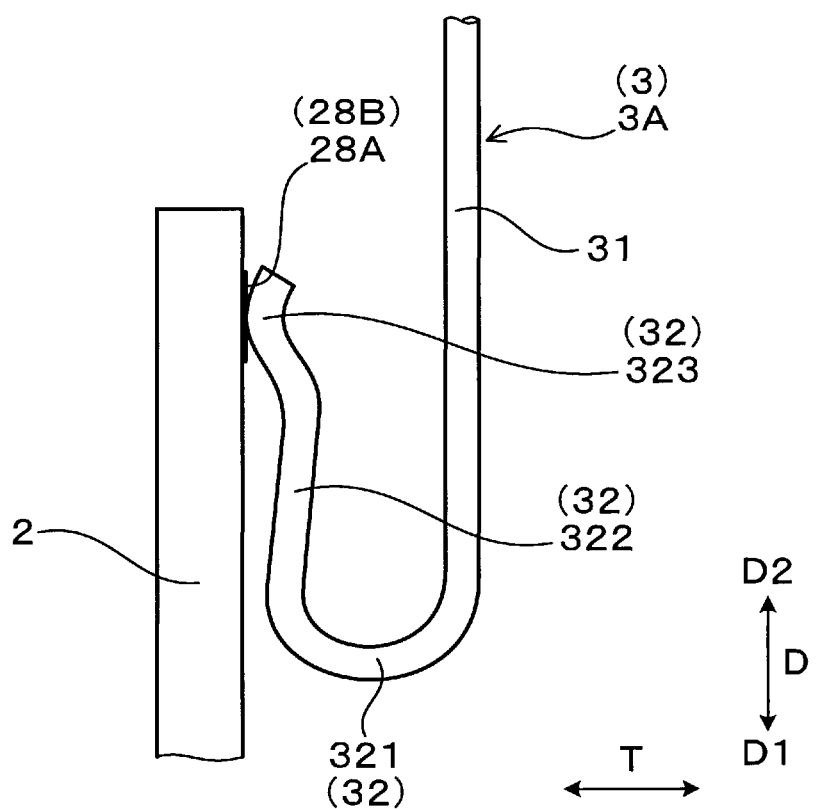
FIG. 20 is an explanatory diagram illustrating a spring terminal that is in contact with a terminal contact portion on a sensor element according to a fourth embodiment.
Figure 21:
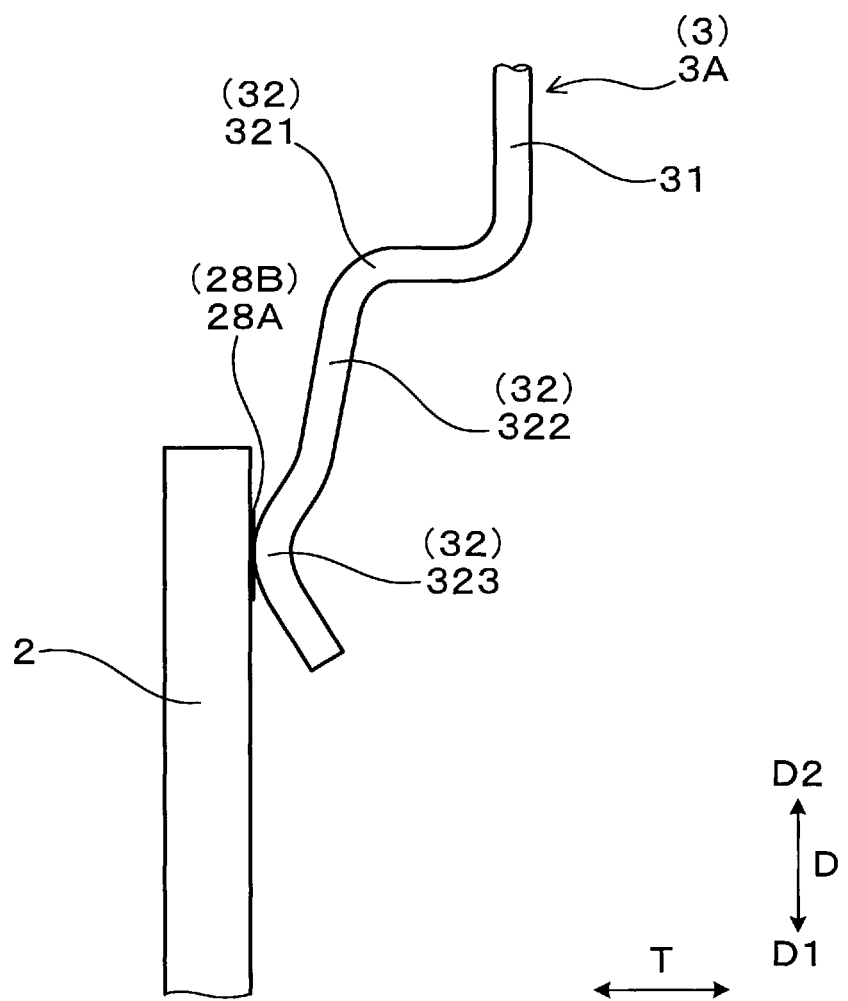
FIG. 21 is an explanatory diagram illustrating another spring terminal that is in contact with the terminal contact portion on the sensor element according to the fourth embodiment.

The holding section 31 of each spring terminal 3 does not necessarily have to be curved so that the position of the holding section 31 in the flexing direction F is offset. Instead, as shown in FIG. 20, the holding sections 31 of the spring terminals 3 may be formed straight to be parallel to the insertion direction D. Each arm section 32 does not necessarily have to be folded back from the holding section 31 in the insertion direction D. Instead, as shown in FIG. 21, the arm section 32 may be formed to extend toward the distal end from the distal end of the holding section 31 in the insertion direction D. Alternatively, although the idea contradicts the intention to reduce the size, as shown in FIG. 22, each arm section 32 may be folded back from the distal end of the holding section 31 in the insertion direction D toward the proximal end and then further folded back toward the distal end.

Figure 22:
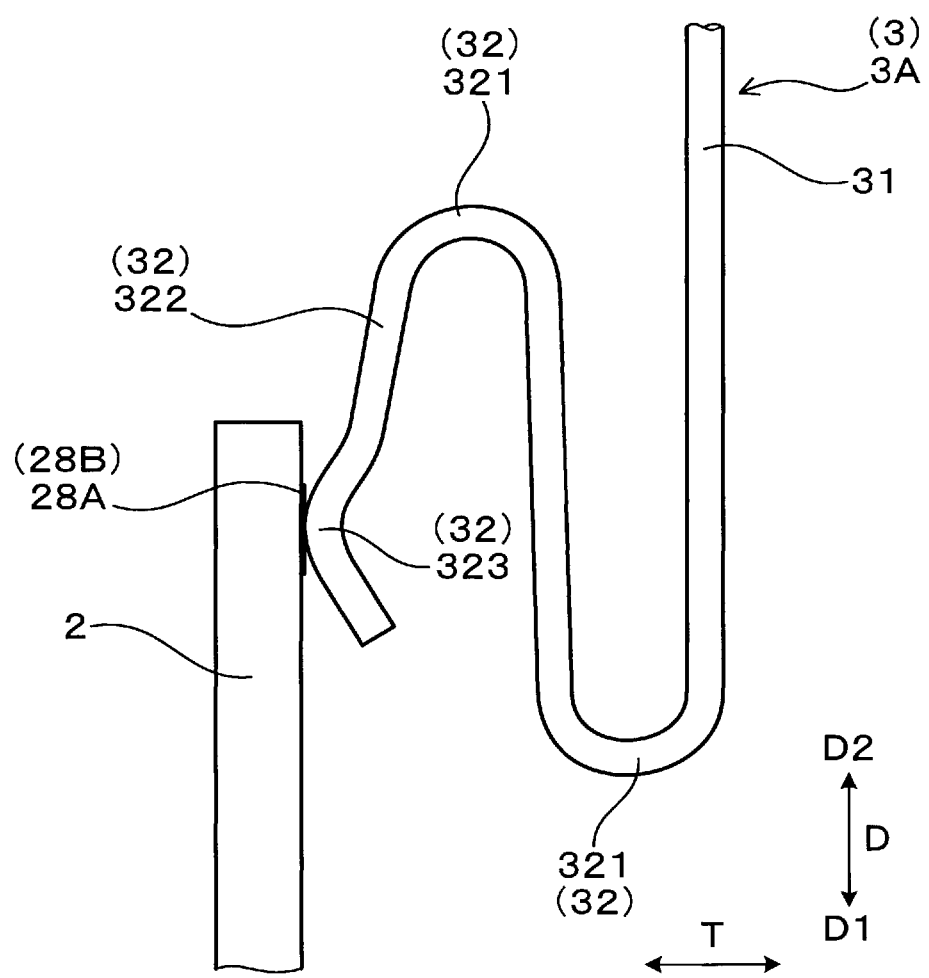
FIG. 22 is an explanatory diagram illustrating another spring terminal that is in contact with the terminal contact portion on the sensor element according to the fourth embodiment.

FIGS. 20 to 22 show the spring terminal 3 located on the outer surface on one side of the sensor element 2. The spring terminals 3 may be located on the outer surfaces on both sides of the sensor element 2.

Other structures and the operational effects of the gas sensor 1 of the present embodiment are the same as those of the first embodiment. In the present embodiment also, the components indicated by the same reference numerals as the reference numerals indicated in the first embodiment are the same as those in the first embodiment.

The number of the spring terminals 3 of the gas sensor 1 may be changed as required in accordance with the number of the electrodes located on the sensor element 2. Two solid electrolytes 21 may be used in the gas sensor 1. The solid electrolyte 21 on which the pumping electrode is formed may be different from the solid electrolyte 21 on which the monitor electrode and the sensor electrode are formed. The structure illustrated in each of the embodiments may be applied to the sensor element 2 without the air duct 27.

The present disclosure is not limited to each of the embodiments, but may configure a different embodiment without departing from the gist of the invention. The present disclosure embraces various variations and variations that come within the scope of equivalent. Furthermore, various combinations and forms of components conceivable from the present disclosure are included in the technical sprits of the present disclosure.

What is claimed is:

1. A gas sensor comprising:
a sensor element for detecting gas, including a plurality of terminal contact portions located on outer surfaces of a proximal section of the sensor element;
a plurality of spring terminals formed of bendable wire; and
an insulator including an insertion hole in which the proximal section of the sensor element is inserted and a plurality of retaining grooves, which communicate with the insertion hole, wherein
each spring terminal includes a holding section, which is retained in the associated retaining groove, and an arm section, which extends from the holding section and is in contact with the associated terminal contact portion while flexing with respect to the holding section,
as viewed in an insertion direction of the sensor element into the insertion hole, at least one of the spring terminals includes an inclined spring terminal, and a flexing direction of the arm section of the inclined spring terminal with respect to the holding section is inclined with respect to an outer surface of the associated terminal contact portion,
the terminal contact portions are located side by side in a widthwise direction orthogonal to the insertion direction,
a plurality of the inclined spring terminals are located side by side in the widthwise direction,
the arm sections of the inclined spring terminals are located closer to a center than the holding sections in the widthwise direction of the sensor element,
the arm section of each inclined spring terminal flexes with an inclination angle of a central axis extending along the flexing direction with respect to a normal perpendicular to the outer surfaces of the terminal contact portions being increased and is in contact with a side surface of the associated retaining groove located at a center side in the widthwise direction, the position of the arm section with respect to the outer surface of the associated terminal contact portion is fixed, and the inclination angle is within a range of 5° or more and 45° or less, and
an angle of a retaining groove, from the plurality of retaining grooves, with respect to a line perpendicular to the outer surfaces of the terminal contact portions of the sensor element is a smaller angle than the inclination angle of the associated arm section of the inclined spring terminal.

2. The gas sensor according to claim 1, wherein
the terminal contact portions are located on opposite sides of the sensor element in a thickness direction orthogonal to both of the insertion direction and the widthwise direction orthogonal to the insertion direction, and
the inclined spring terminals are located at positions facing each other with the sensor element located in between.

3. The gas sensor according to claim 1, wherein
the inclined spring terminals include a pair side by side in the widthwise direction on a first side of the sensor element in a thickness direction and another pair side by side in the widthwise direction on a second side of the sensor element in the thickness direction, and
the plurality of spring terminals includes a vertical spring terminal, which is a spring terminal other than the inclined spring terminals, and the vertical spring terminal is located between the pair of the inclined spring terminals located side by side in the widthwise direction, and the flexing direction of the arm section of the vertical spring terminal is perpendicular to the outer surface of the associated terminal contact portion.

4. The gas sensor according to claim 1, wherein
the sensor element includes a solid electrolyte on which at least a pair of electrodes are located and a heater laminated on the solid electrolyte, and
the plurality of terminal contact portions include a first terminal contact portion, which is connected to the pair of electrodes, and a second terminal contact portion, which is connected to a heating element of the heater.

5. The gas sensor according to claim 1, wherein each arm section is folded back from the associated holding section to face the associated holding section.

6. The gas sensor according to claim 1, wherein
a cross-sectional shape of the spring terminals includes a flat shape, an elliptic shape, or an angular shape including a rectangular shape, and
an aspect ratio of a cross-section of the spring terminals is in the range of 1:1 to 1:2.

7. The gas sensor according to claim 1, wherein the plurality of the inclined spring terminals located side by side in the widthwise direction are arranged at positions and with the inclination angle such that when the sensor element is not inserted in the insertion hole of the insulator, the arm sections of the inclined spring terminals do not come into contact with each other.

8. The gas sensor according to claim 1, wherein at least two of the retaining grooves, among the plurality of retaining grooves, are formed to incline with respect to a thickness direction of the sensor element so that the spring terminals are arranged in an inclined state with respect to the thickness direction and the spring terminals are arranged to a radial pattern in the insulator as viewed from the insertion direction.

9. The gas sensor according to claim 1, wherein the line perpendicular to the sensor element extends away from the sensor element.

10. The gas sensor according to claim 1, wherein the line perpendicular to the sensor element includes the normal perpendicular to the outer surface of the associated terminal contact portion of the sensor element.

11. A gas sensor comprising:
a sensor element for detecting gas, including a plurality of terminal contact portions located on outer surfaces of a proximal section of the sensor element;
a plurality of spring terminals formed of bendable wire; and
an insulator including an insertion hole in which the proximal section of the sensor element is inserted and a plurality of retaining grooves, which communicate with the insertion hole, wherein
each spring terminal includes a holding section, which is retained in the associated retaining groove, and an arm section, which extends from the holding section and is in contact with the associated terminal contact portion while flexing with respect to the holding section, and
as viewed in an insertion direction of the sensor element into the insertion hole, at least one of the spring terminals includes an inclined spring terminal, and a flexing direction of the arm section of the inclined spring terminal with respect to the holding section is inclined with respect to an outer surface of the associated terminal contact portion, the plurality of spring terminals are formed of round wire having a circular cross-section and a wire diameter within a range of φ 0.4 mm or more and 0.7 mm or less, and an angle of a retaining groove, from the plurality of retaining grooves, with respect to a line perpendicular to the outer surfaces of the terminal contact portions of the sensor element is a smaller angle than an inclination angle of the associated arm section of the inclined spring terminal, the inclination angle being of a central axis extending along the flexing direction with respect to a normal perpendicular to the outer surfaces of the terminal contact portions, wherein the inclination angle is within a range of 5° or more and 45° or less.

12. The gas sensor according to claim 11, wherein at least two of the retaining grooves, among the plurality of retaining grooves, are formed to incline with respect to a thickness direction of the sensor element so that the spring terminals are arranged in an inclined state with respect to the thickness direction and the spring terminals are arranged to a radial pattern in the insulator as viewed from the insertion direction.

13. The gas sensor according to claim 11, wherein the line perpendicular to the sensor element extends away from the sensor element.

14. The gas sensor according to claim 11, wherein the line perpendicular to the sensor element includes the normal perpendicular to the outer surface of the associated terminal contact portion of the sensor element.

* * * * *